US010765868B2

(12) United States Patent
Chang et al.

(10) Patent No.: US 10,765,868 B2
(45) Date of Patent: Sep. 8, 2020

(54) ELECTRICAL STIMULATION DEVICE

(71) Applicant: GiMer Medical Co., Ltd., New Taipei (TW)

(72) Inventors: Chi-Heng Chang, New Taipei (TW); Jian-Hao Pan, New Taipei (TW)

(73) Assignee: GIMER MEDICAL CO., LTD, New Taipei (TW)

( * ) Notice: Subject to any disclaimer, the term of this patent is extended or adjusted under 35 U.S.C. 154(b) by 72 days.

(21) Appl. No.: 15/299,723

(22) Filed: Oct. 21, 2016

(65) Prior Publication Data

US 2017/0113047 A1  Apr. 27, 2017

(30) Foreign Application Priority Data

Oct. 23, 2015  (CN) .......................... 2015 1 0694416
May 16, 2016  (CN) .......................... 2016 1 0323066

(51) Int. Cl.
*A61N 1/36* (2006.01)

(52) U.S. Cl.
CPC ....... *A61N 1/3615* (2013.01); *A61N 1/36071* (2013.01); *A61N 1/36125* (2013.01); *A61N 1/36153* (2013.01); *A61N 1/36171* (2013.01); *A61N 1/36142* (2013.01)

(58) Field of Classification Search
CPC .. A61N 1/36; A61N 1/36071; A61N 1/36014; A61N 1/3615; A61N 1/36153; A61N 1/36171; A61N 1/36125; A61N 1/36142; A61N 1/40
USPC .......................................................... 607/46
See application file for complete search history.

(56) References Cited

U.S. PATENT DOCUMENTS

| | | | |
|---|---|---|---|
| 4,088,141 A | | 5/1978 | Niemi |
| 4,400,590 A | * | 8/1983 | Michelson ......... A61N 1/36036 381/320 |
| 4,759,368 A | | 7/1988 | Spanton et al. |
| 5,601,608 A | * | 2/1997 | Mouchawar ......... A61N 1/3956 607/13 |

(Continued)

FOREIGN PATENT DOCUMENTS

| | | | | |
|---|---|---|---|---|
| TW | M498025 U | * | 4/2015 | ............... A61N 1/18 |
| TW | M498025 U | | 4/2015 | |

*Primary Examiner* — Mallika D Fairchild
*Assistant Examiner* — Minh Duc G Pham
(74) *Attorney, Agent, or Firm* — Muncy, Geissler, Olds & Lowe, P.C.

(57) ABSTRACT

The present application discloses am electrical stimulation device for electrically stimulating at least one target zone of an organism. The electrical stimulation device comprises a control unit and an electrical stimulation unit. The electrical stimulation unit includes a frequency synthesizer, an amplifier, a variable resistor, at least one first electrode and at least one second electrode. The frequency synthesizer is coupled to the control unit and generates a frequency signal. The amplifier is coupled to the frequency synthesizer. The variable resistor comprises a resistance and is coupled to the control unit and the amplifier. The first electrode and the second electrode are coupled to the amplifier. The amplifier outputs an electrical stimulation signal according to the frequency signal of the frequency synthesizer and the resistance of the variable resistor to impel the first electrode and the second electrode to generate an electric field.

19 Claims, 20 Drawing Sheets

(56) References Cited

U.S. PATENT DOCUMENTS

| | | | |
|---|---|---|---|
| 2005/0245994 A1* | 11/2005 | Varrichio | A61N 1/14 607/60 |
| 2011/0071589 A1 | 4/2011 | Starkebaum et al. | |
| 2012/0029591 A1 | 3/2012 | Simon et al. | |
| 2016/0008602 A1* | 1/2016 | Perryman | H02J 50/20 607/61 |
| 2016/0096022 A1* | 4/2016 | Lin | A61N 1/36071 607/46 |

* cited by examiner

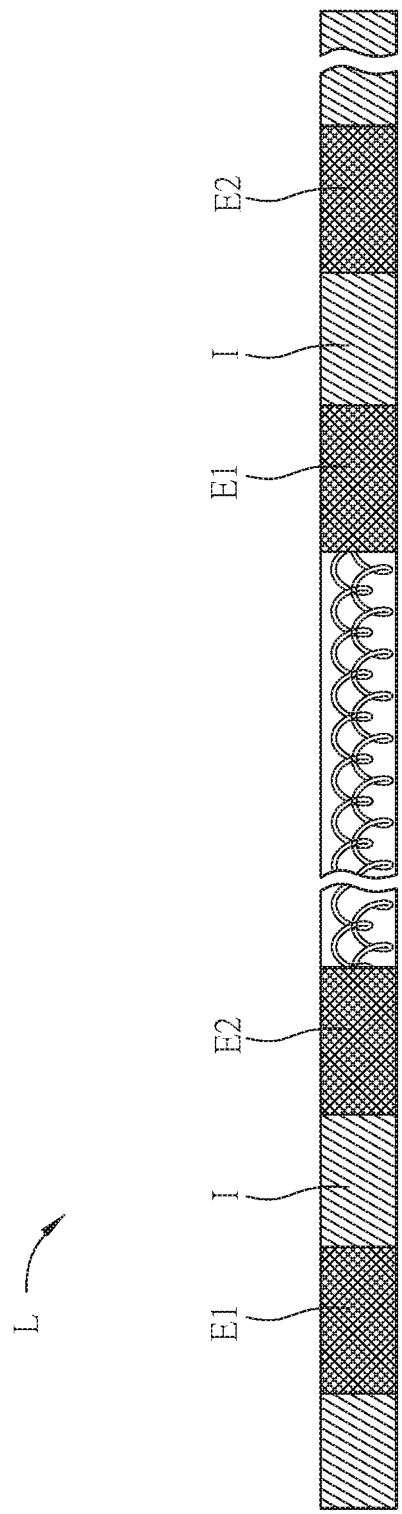

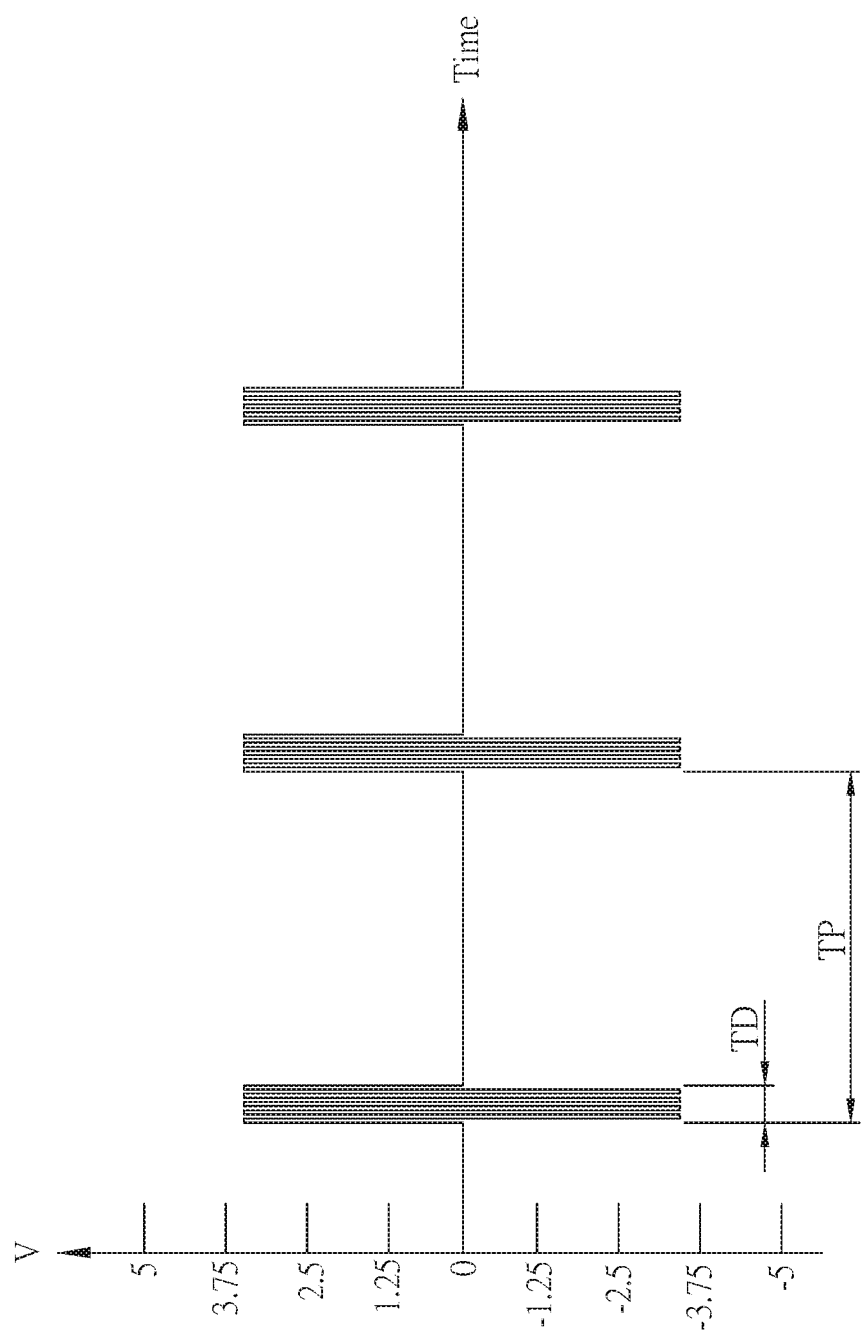

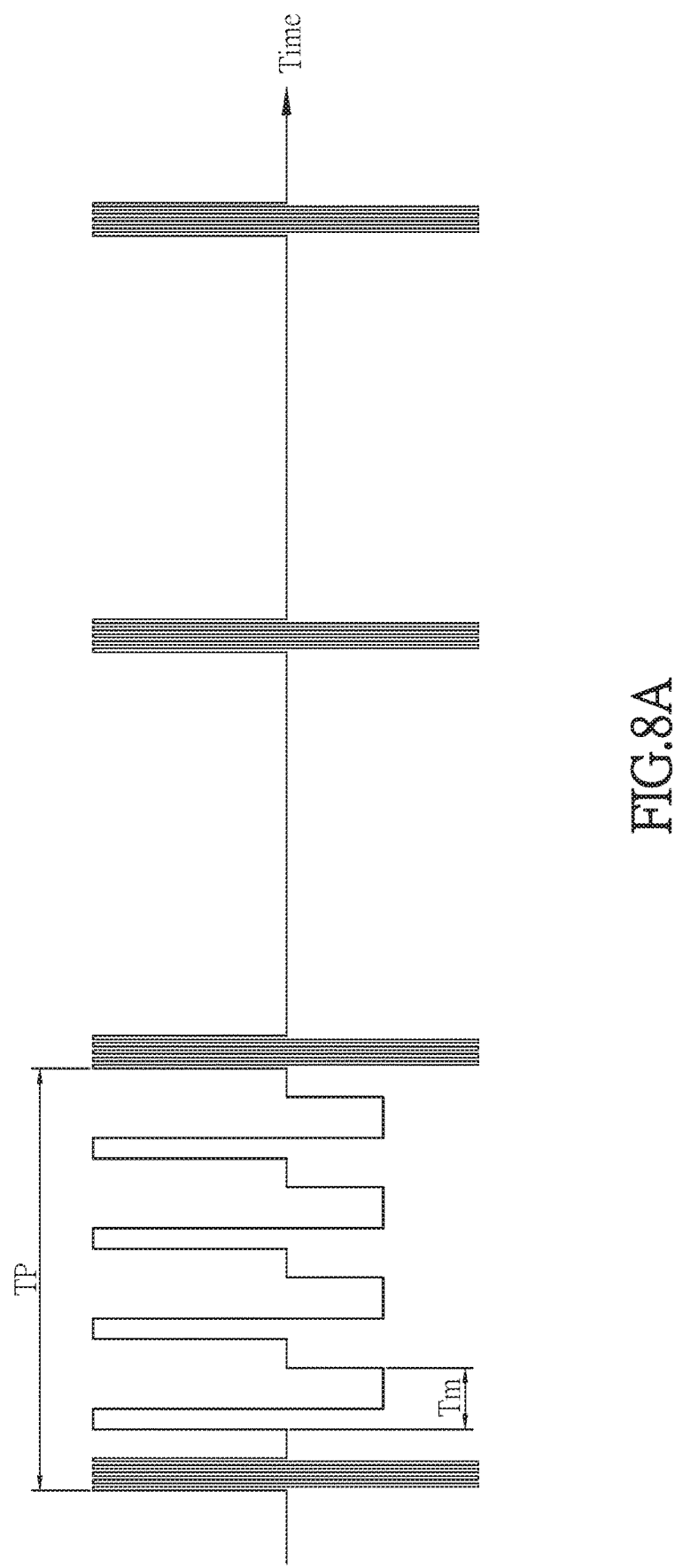

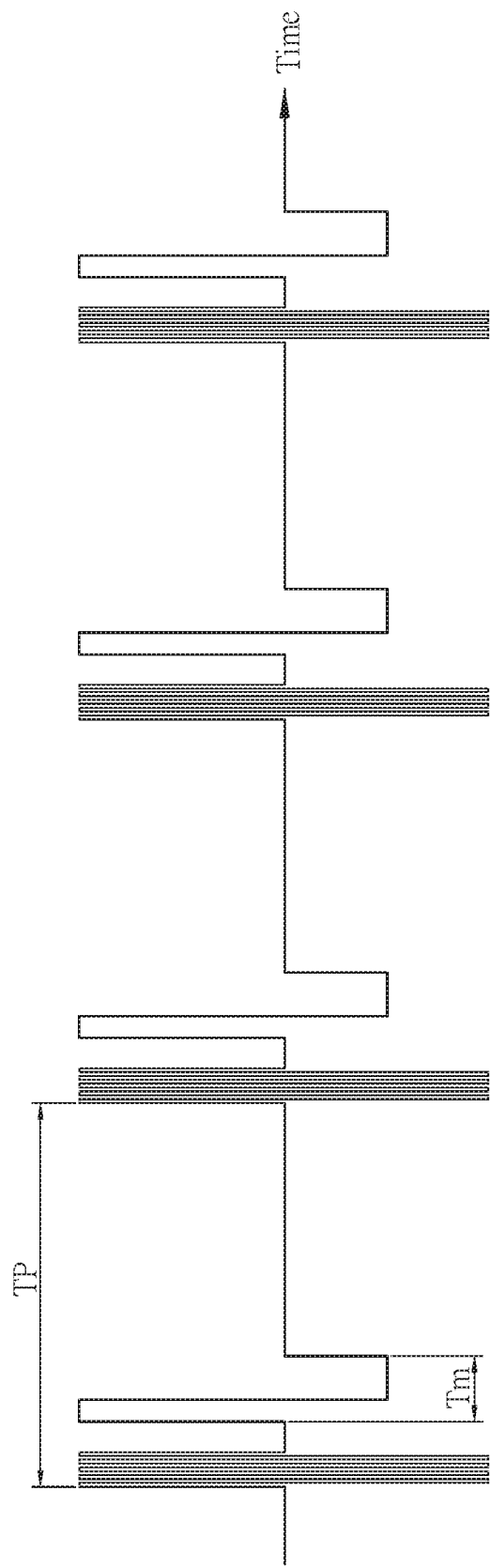

ELECTRICAL STIMULATION DEVICE

CROSS REFERENCE TO RELATED APPLICATIONS

This Non-provisional application claims priority under 35 U.S.C. § 119(a) on Patent Application No(s). 201510694416.2 and 201610323066.3 filed in People's Republic of China on Oct. 23, 2015 and May 16, 2016, the entire contents of which are hereby incorporated by reference.

BACKGROUND

Technical Field

The present invention relates to an electrical stimulation device.

Related Art

The human nerves are mainly used as the conduction path of the instructions (current) issued by the brain. Human nerves have a threshold, which is usually decreased when the nerves get damages. Accordingly, the human body will be susceptible to the pain of the nerve injury portion. If the nerve damage doesn't have timely and properly treatment, a chronic pain disease of this nerve injury portion will be incurred.

Electrical stimulation is a common treatment for relieving pain in patients of chronic pain disease. Generally, the patient temporary reliefs of pain after the electrical stimulation treatment, but this comfort can't last for a long time. Thus, the patient needs frequent electrical stimulation treatments in order to maintain the comfortable state.

In addition, with the improvement of electrical stimulation technology, the electrical stimulation methods are developed for different symptoms. For example, the spinal nerve electrical stimulation can be used to treat paralysis and the likes. The cerebral cortical electrical stimulation can be used to treat Parkinson's disease. The bladder nerve stimulation can be used to solve the problem that the stroke and paralysis patient can't spontaneous urination, thereby avoiding the possible complications. The retinal nerve stimulation can help the blind patients to re-feel the weak light and have rough sight. For different applications, the electrical stimulation signals may require different electric fields, voltages, currents, durations and frequencies.

SUMMARY

An aspect of the disclosure is to provide an electrical stimulation device for electrically stimulating at least one target zone of an organism. The electrical stimulation device comprises a control unit and an electrical stimulation unit. The electrical stimulation unit includes a frequency synthesizer, an amplifier, a variable resistor, at least one first electrode and at least one second electrode. The frequency synthesizer is coupled to the control unit and generates a frequency signal. The amplifier is coupled to the frequency synthesizer. The variable resistor comprises a resistance and is coupled to the control unit and the amplifier. The first electrode and the second electrode are coupled to the amplifier. The amplifier outputs an electrical stimulation signal according to the frequency signal of the frequency synthesizer and the resistance of the variable resistor to impel the first electrode and the second electrode to generate an electric field. The electric field covers the target zone, and the electric field strength ranges from 100 V/m to 5000 V/m, so as to electrically stimulate the target zone of the organism.

In one embodiment, the first electrode and the second electrode are coupled to a mixer. The electrical stimulation signal impels the first electrode and the second electrode to generate an electric field. The electric field covers the target zone, and the electric field strength ranges from 100 V/m to 5000 V/m.

In one embodiment, the frequency synthesizer is coupled to an input of the amplifier.

In one embodiment, the variable resistor is coupled to the input of the amplifier.

In one embodiment, the variable resistor is coupled to an output of the amplifier.

In one embodiment, the electrical stimulation unit further comprises a filter which is coupled between the frequency synthesizer and the amplifier.

In one embodiment, the electrical stimulation unit further comprises a detector which is coupled to the control unit and the amplifier and detects the electrical stimulation signal.

In one embodiment, the electrical stimulation unit further comprises a surge protector which is coupled to the amplifier.

In one embodiment, the electrical stimulation device is an implanted electrical stimulation device.

In one embodiment, the frequency of the electrical stimulation signal ranges from 200 KHz to 1000 KHz.

In one embodiment, the voltage of the electrical stimulation signal is biphasic, and its absolute value is between 3V and 12V.

In one embodiment, the second pulse wave signal is substantially a delay signal of the first pulse wave signal.

In one embodiment, the amplitude of the first wave signal does not equals to that of the second wave signal.

In one embodiment, there is a time difference between the first pulse wave signal and the second pulse wave signal.

An aspect of the disclosure is to provide a method applied to electrically stimulate a target zone of an organism by an implanted electrical stimulation device. The implanted electrical stimulation device comprises a frequency synthesizer, a variable resistor and at least a first electrode and at least a second electrode. The method comprises the following steps. A frequency signal is generated by the frequency synthesizer. An electrical stimulation signal is outputted according to the frequency signal and the resistance of the variable resistor. And, the electrical stimulation signal is delivered by the first electrode and the second electrode to generate an electrical field between the first electrode and the second electrode to electrically stimulate the target zone. The electric field covers the target zone, and the strength of the electric field ranges from 100 V/m to 5000 V/m.

In one embodiment, the frequency of the electrical stimulation signal ranges from 200 KHz to 1000 KHz.

In one embodiment, the method further comprises the following steps. A first pulse wave signal and a second pulse wave signal are generated and a biphasic pulse signal is outputted according to the plurality of first pulse wave signal and the second pulse wave signal. The amplifier outputs the electrical stimulation signal according to the biphasic pulse signal, and the frequency signal and the resistance of the variable resistor. The difference between the integrated value of the amplitude of the first pulse wave signal with respect to time and the integrated value of the amplitude of the second pulse wave signal with respect to time is not more than ten percent of the integrated value of the amplitude of the first pulse wave signal with respect to time In one embodiment, the second pulse wave signal is substantially a delay signal of the first pulse wave signal.

In one embodiment, the amplitude of the first wave signal does not equals to that of the second wave signal.

In one embodiment, there is a time difference between the first pulse wave signal and the second pulse wave signal.

Accordingly, the electrical stimulation device balances the charges of the electrical stimulation signal through a synthesized signal with interleaving positive phases and negative phases, so as to reduce the possibility that the electrical stimulation signal may damage the targeted nerve. The electrical stimulation device can provide electrical stimulation signals with different characteristics to the patient, so as to carry out appropriate electrical stimulation therapy, according to different needs.

BRIEF DESCRIPTION OF THE DRAWINGS

The embodiments will become more fully understood from the detailed description and accompanying drawings, which are given for illustration only, and thus are not limitative of the present invention, and wherein:

FIGS. 1C and 1D are enlarged diagrams showing a lead of the electrical stimulation unit in FIG. 1A;

FIG. 3C is a schematic diagram showing the waveform of the frequency signal generated by the electrical stimulation device according to one embodiment;

FIGS. 8A to 8D are schematic diagrams showing the waveforms of the electrical stimulation signal according to various embodiments.

DETAILED DESCRIPTION OF THE INVENTION

The embodiments of the invention will be apparent from the following detailed description, which proceeds with reference to the accompanying drawings, wherein the same references relate to the same elements.

In order to make the structure of the present device easier to be understood in relation to other cooperating devices in practice, the configuration of the electrical stimulation device for electrical stimulation of the target zone of the organism and the circuit configuration of the controller and the coordination with each other are described as follows.

Figure 1A:
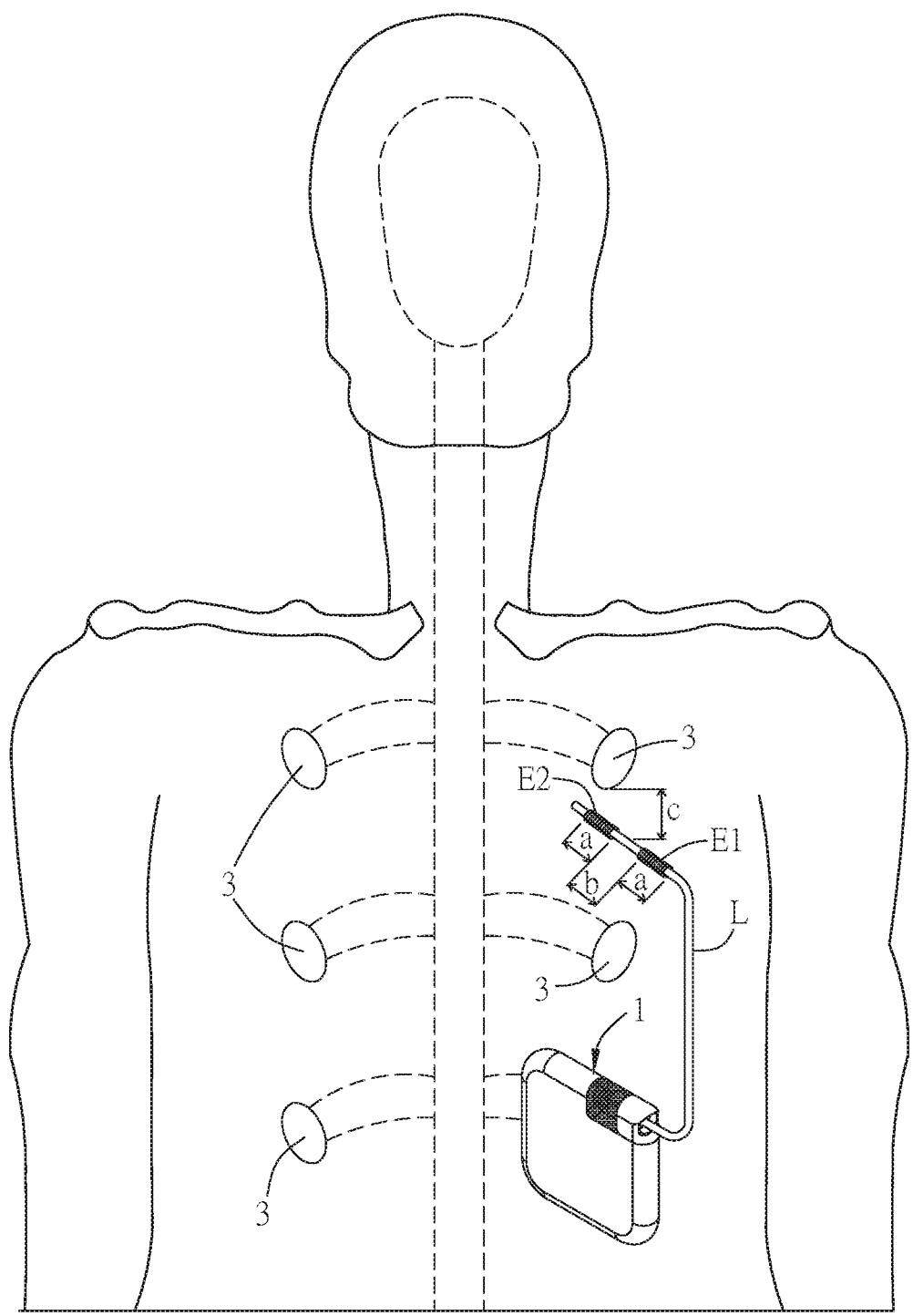
FIG. 1A is a schematic diagram showing the electrical stimulation device applied to the dorsal root ganglion according to the first embodiment.

As shown in FIG. 1A, the electrical stimulation device 1 may be installed outside the individual or at least partially implanted inside the individual for electrical stimulation therapy, and the electrical stimulation device 1 is preferably a stimulation device for electrically stimulating a nerve, such as a spinal dorsal root ganglion. The stimulated target region may be, for example, but not limited to, applied to the brain, vertebral column, and/or spinal dorsal horn, epidural space of an organism. The above-mentioned vertebral column can be the ninth thoracic nerve (T9 vertebrae) and the tenth thoracic nerve (T10 vertebrae). An individual referred hereinafter can be an organism and includes mammals, such as mice, humans, rabbits, cattle, sheep, pigs, monkeys, dogs, cats and the like, preferably humans. The electric stimulation device 1 includes a control unit 11 and an electrical stimulation unit 12. As an example, the electric stimulation unit 12 of the electrical stimulation device 1 is at least partially implanted into the human body, and the electrodes of the electrical stimulation unit 12 (the first electrode E1, the second electrode E2) are implanted in near the dorsal root ganglion 3 for electrical stimulation.

Figure 1B:
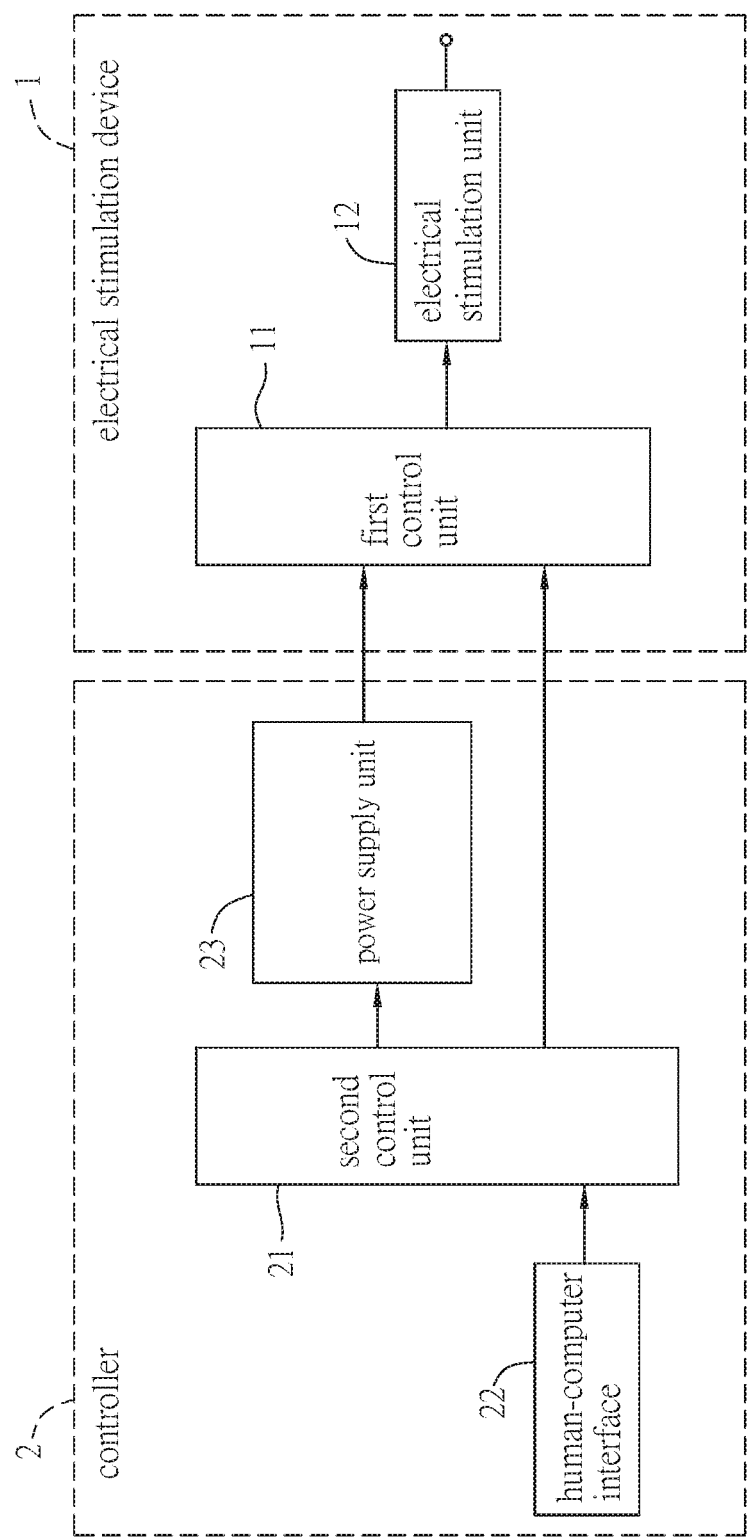
FIG. 1B is a circuit block diagram of the electrical stimulation device and the controller in FIG. 1A.
Figure 1D:
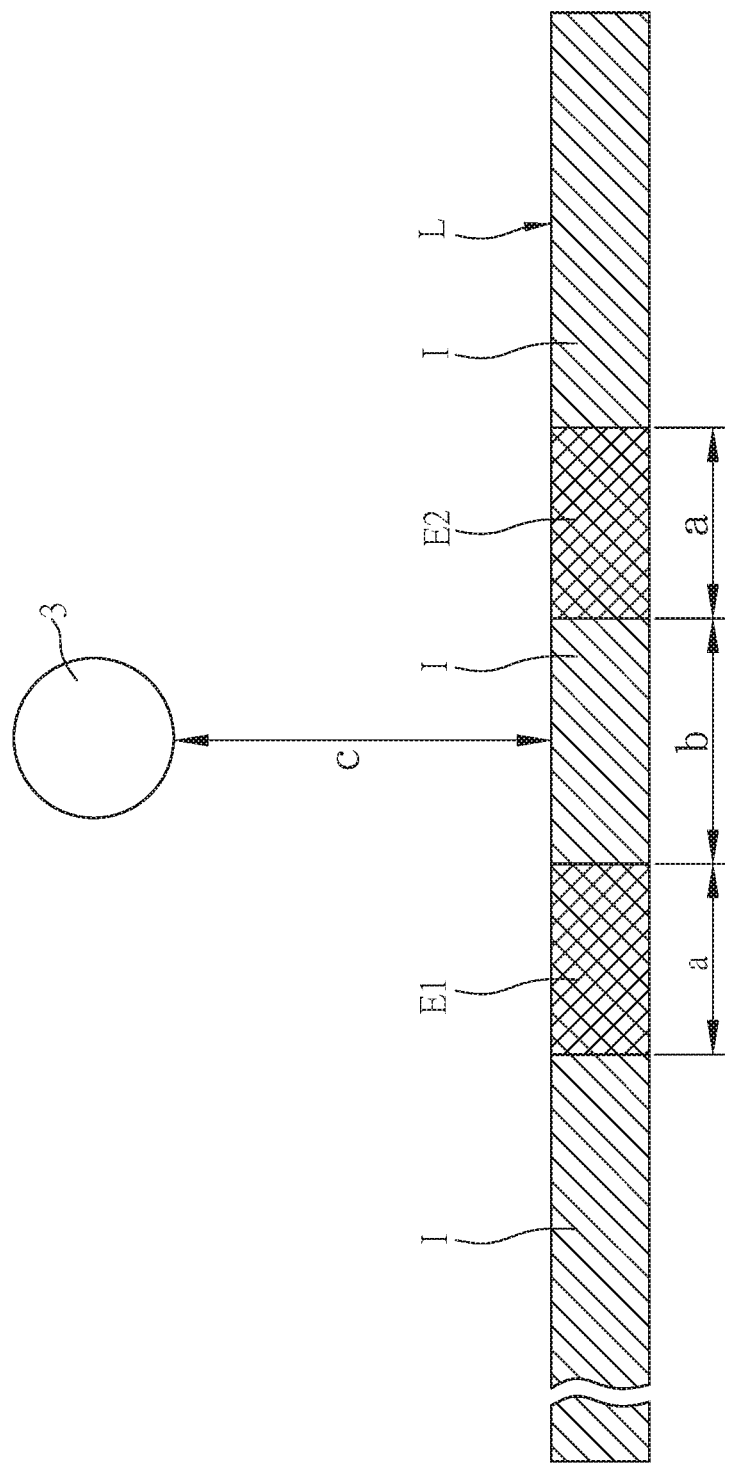

FIG. 1B is a circuit block diagram of the electrical stimulation device 1 and its associated controller 2. As shown in FIG. 1B, a controller 2 provides configuration parameters and supplies energy for the electronic stimulation device 1. Because the controller 2 does not need to be implanted in the organism, it may be called an external controller. Elements of the electronic stimulation device 1 and the controller 2 and their relationships will be described in the following paragraphs.

The electrical stimulation device 1 comprises a control unit 11 and an electrical stimulation unit 12. The electrical stimulation unit 12 is coupled to the control unit 11. The controller 2 comprises another control unit 21, a human machine interface 22, and a power supply unit 23. The human machine interface 22 is coupled to the control unit 21, and the power supply unit 23 is also coupled to the control unit 21 and serves as a power source for the controller 2. The power supply unit 23 may be a battery or a rechargeable battery, or may be a power adapter to connect an external mains to supply electrical power.

The user may use the human machine interface 22 to operate the controller 2. Before beginning, the system default values of the controller 2 is initialized. Then, he may also use the human machine interface 22 to input the required configuration parameters to the control unit 21. The human interface 22 may be, for example but not limited to, a touch bottom, a touch panel, a physical bottom, or combination thereof. The control unit 21 instructs the power supply unit 23 to supply the DC power to the elements of the electrical stimulation device 1 (for example the electrical stimulation unit 12) to operation. The control unit 11 and the control unit 21 may be implemented with digital circuit such as an integrated circuit (IC) or implemented with analog circuit. For example, IC may be a micro-processor, a MCU, a programmable logic gate array (for example FPGA or CPLD), or an application specific integrated circuit (ASIC). In the present embodiment, it is a microcontroller (MCU) for example, but the present invention is not limited thereto.

As to the configuration of the electrical stimulation unit 12, referring to FIGS. 1A to 1D, the electrical stimulation unit 12 includes a flexible lead L that includes at least one first electrode E1 and at least one second electrode E2. In the present embodiment, it includes a pair of electrodes. That is, the first electrode E1 is a positive electrode and the second electrode E2 is a negative electrode. In addition, the number of electrodes provided on the lead L may be two or more, and may be evenly distributed on the lead L of the electrical stimulation unit 12 or only at the end of the lead L. The electrode is operated in a bi-phase mode to generate an electrical field between the first electrode E1 and the second electrode E2. The electrical field range covers the target zone and the electrical field intensity ranges from 100 V/m to 5000 V/m, so as to electrically stimulate the target zone. In the present embodiment, the material of the first electrode E1 and the second electrode E2 may be metal for example platinum, silver, gold, or other conductive metal. Between the first electrode E1 and the second electrode E2, a zone is defined by the coils or wires which are compactly wound electrically connected to the electrodes. More specifically, the first electrode E1 and the second electrode E2 are disposed at one end of the lead L, and the other end of the lead L has two contacts acting as a positive electrode and a negative electrode. The two contacts are electrically connected or electrically coupled to the control unit 11. The first electrode E1 and the second electrode E2 are respectively linked to compactly wound coils, and they are linked to the contacts through the wires. In addition, the wires of the lead L beyond the first electrode E1 and the second electrode E2 is covered by an insulator I. In FIG. 1C, a portion of the insulator I is removed to show the coil disposed between the electrodes in the lead L.

The ranges of the individual lengths a of each electrode depends on actual or design requirement. The electrode length a is in the range of 0.5 to 6 mm, preferably 1 to 4 mm. The individual length a of the first electrode E1 and the second electrode E2 refers to a length of the electrode in the direction parallel to the extension direction of the major axis of the lead L of the electrical stimulation unit 12. The distance b between the first electrode E1 and the second electrode E2 is 1 to 7 mm, preferably 1 to 4 mm.

A second distance c exists between the first electrode E1 and the second electrode E2 of the lead L and the dorsal root ganglion 3. The second distance c is defined as the shortest distance from the midpoint of the adjacent first electrode E1 and the second electrode E2 to the dorsal root ganglion 3. In the present embodiment, the distance c is in the range of 0 to 10 mm. When the distance c is 0 mm, the middle point of the first electrode E1 and the second electrode E2 in the projection direction overlaps the dorsal root ganglion 3.

In the embodiment, the electric stimulation device 1 is an active electrical stimulation device of which the control unit 11 together with the electrical stimulation unit 12 are implanted in the target zone (the dorsal root ganglion) of organism. In other words, the control unit 11 and the electrical stimulation unit 12 are implanted subcutaneously in the organism. Alternatively, the control unit 11 and the electrical stimulation unit 12 are integrated into one part first and then implanted subcutaneously. Because of electrically coupled to the controller 2 outside the organism, the first control unit 11 can receive the parameter signal and the electric energy from the second control unit 21 so that the electrical stimulation unit 12 may electrically stimulate the target zone of the organism.

Figure 2A:
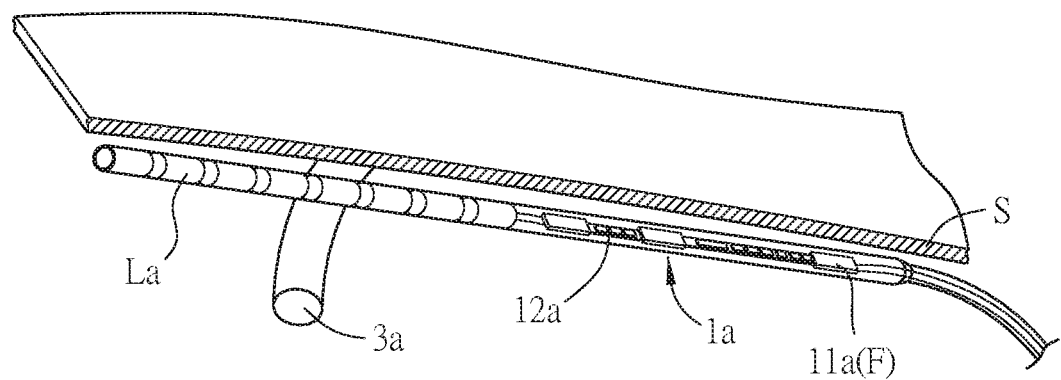
FIGS. 2A and 2B are schematic diagrams showing the electrical stimulation device according to another embodiment.

It should be noted that the electrical stimulation device is not limited to the above-mentioned electrical stimulation device 1. In other embodiments, the active electrical stimulation device may be like the electrical stimulation device in FIG. 2A. The electric stimulation device 1a in the present embodiment and the electrical stimulation device 1 have substantially alike elements thereof, and the first control unit 11a and the electric stimulation unit 12a are also respectively implanted in the epidermis S of the organism (subcutaneous). The first control unit 11a of the electric stimulation device 1a of the present embodiment is a flexible circuit board (FPCB) integrated in the electrical stimulation unit and it still can receive the parameter signal and electrical energy from the second control unit (not shown) outside the organism. The lead La of the electric stimulation unit 12a can electrically stimulate the subcutaneous nerve 3a of the organism. The electrical stimulation device 1a of the present embodiment may reduce its volume enough to be implanted subcutaneously for abating the burden of the organism (or the patient).

Figure 2B:
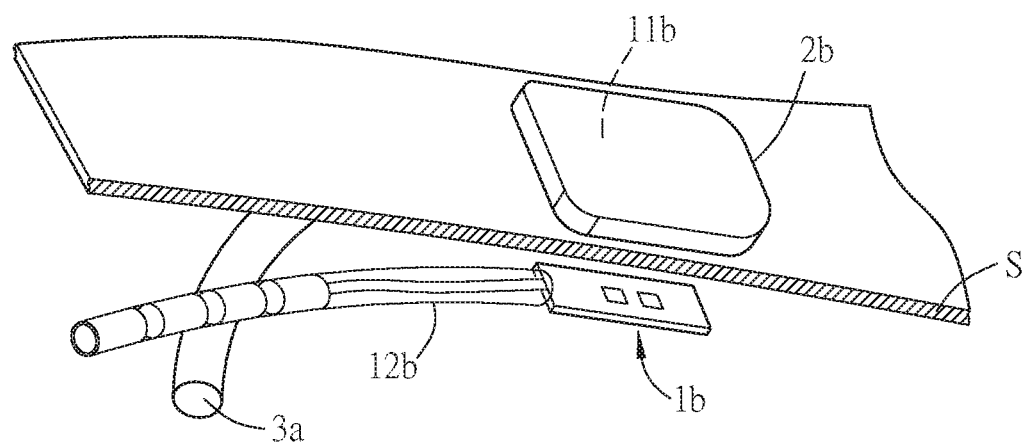

Alternatively, the electrical stimulation device may be like the device shown in FIG. 2B. As shown in FIG. 2B, the electrical stimulation device 1b of the present embodiment is a passive electrical stimulation device, which is different from the electrical stimulation device 1 of the foregoing embodiment in that the control unit 11b of the electrical stimulation device 1b is integrated into the controller 2b disposed outside the epidermis S of the organism. Thus, the implanted electrical stimulation device 1b does not contain a control unit therein. The electrical stimulation unit 11b at its end has a flexible circuit board (FPCB) which is implanted subcutaneously and not deeply (e.g., less than 5 cm in depth), so as to transmit an electrical stimulation signal to the lead L2 through the external controller 2b that is not implanted in the skin, and the electrical stimulation unit 12b can passively and electrically stimulate the subcutaneous nerve 3a of the organism.

Figure 3A:
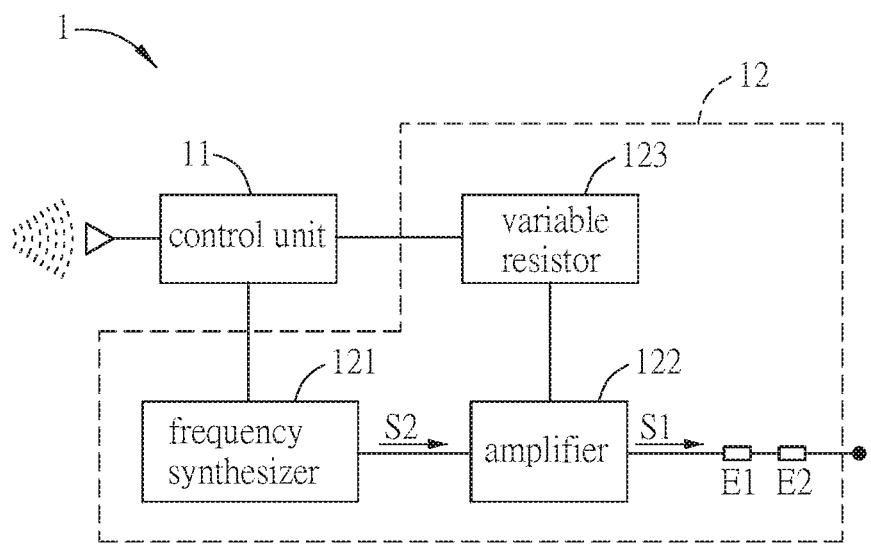
FIG. 3A is a schematic diagram showing the electrical stimulation device according to one embodiment.

As shown in FIG. 3A, which is a schematic block diagram of a preferred embodiment of the electrical stimulation device of the present invention. The electrical stimulation device 1 includes a control unit 11 and an electrical stimulation unit 12. The control unit 11 may store electrical stimulation parameters and electrical stimulation data and act upon the data and parameters to control the electrical stimulation unit 12. The electrical stimulation unit 12 includes a pulse generator 120, a frequency synthesizer 121, an amplifier 122, and a variable resistor 123. The electrical stimulation unit 12 may receive an instruction from the control unit 11 to output the electrical stimulation signal S1 to the subject for electrical stimulation therapy. The voltage of the electrical stimulation signal S1 is biphasic to reduce the possibility that the electrical stimulation therapy may damage the nerve. Its absolute value ranges from 3 V to 12 V. For example, the electrical stimulation signal S1 may be an alternating current with an amplitude ranging from 3 V to 12 V. Further, the frequency synthesizer 121 is coupled to the control unit 11 and generates a frequency signal S2 whose frequency is greater than 100 kHz in accordance with the control of the control unit 11. In this embodiment, the frequency synthesizer 121 is a direct digital synthesizer as an example. For example, the direct digital synthesizer can be AD9833 of Analog Devices, Inc. AD 9833 can output sine, square, or triangular waves with a maximum output frequency of 12.5 MHz and a maximum output voltage of approximately 650 mV. Of course, the frequency synthesizer 121 is not limited to the above-mentioned type, so long as the frequency synthesizer 121 can generate the high-frequency signal S2 and output the high-frequency electrical stimulation signal S1. However, in another embodiment, the frequency synthesizer 121 may also be integrated into the control unit 11 (not shown). In other words, such electrical stimulation unit 12 includes only the pulse generator 120, the amplifier 122, and the variable resistor 123.

It should be noted that the electrical stimulation device of the present invention can be driven by current or voltage. For the sake of convenience of explanation, the following paragraphs describe a voltage-driving electrical stimulation device as an embodiment. However, in a same circuit architecture, the amplifier 122 may also convert the voltage signal into a current signal to cause the electrical stimulation device to be driven by current. The present invention is not limited thereto.

Figure 3B:
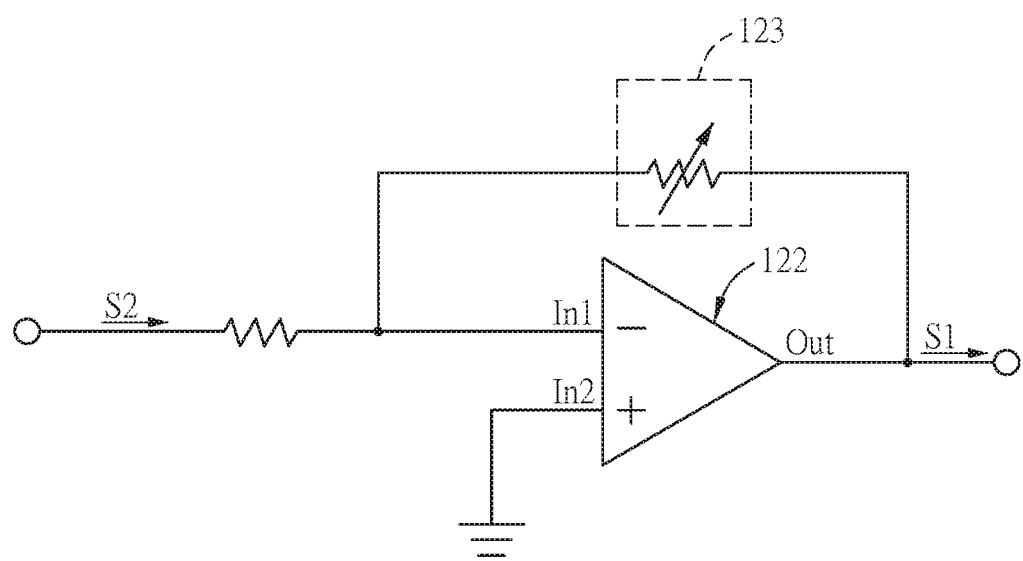
FIG. 3B is a circuit block diagram of the amplifier of the electrical stimulation device according to one embodiment.

Please also refer to FIG. 3B, which is a circuit diagram of the amplifier. In the present embodiment, the amplifier 122 is coupled to the frequency synthesizer 121. The amplifier 122 is an operational amplifier (OPA) and includes an inverting input terminal In1, a non-inverting input terminal In2, and an output terminal Out. The frequency synthesizer 121 is coupled to one of the inputs (inverting input In1 or non-inverting input In2) of the amplifier 122. In the present embodiment, the inverting input In1 is coupled to the frequency synthesizer 121 and the input In12 is grounded. In this way, since the output voltage of the frequency synthesizer 121 is lower (about 650 mV), the voltage of the frequency signal S2 output from the frequency synthesizer 121 is amplified to 3 V to 12 V by the amplifier 122 so as to conform to the above-mentioned voltage setting of the signal S1.

The variable resistor 123 may be a digital potentiometer (digiPOT), and has a resistance value. The variable resistor 123 is coupled to the control unit 11 and the amplifier 122. For example, the variable resistor 123 can be AD5290 of Analog Devices, Inc., which is a 10 kΩ digital variable resistor. The control unit 11 adjusts the resistance value of the variable resistor 123 in accordance with the electric stimulation parameter. Accordingly, the resistance value is not a fixed value. Thus, the amplifier 122 outputs the electrical stimulation signal S1 according to the frequency signal S2 of the frequency synthesizer 121 and the resistance value of the variable resistor 123. The frequency of the electrical stimulation signal S1 is determined by the frequency signal S2 of the frequency synthesizer 121. For example, the frequency can be greater than 100 kHz, such as 200 kHz to 1000 kHz. The voltage of the electrical stimulation signal S1 is determined by the amount of gain of the amplifier 122, and the resistance value of the variable resistor 123 affects the gain of the amplifier 122. It is to be noted that the frequency signal S2 is preferably in the range of 200 kHz to 250 kHz, 250 kHz to 350 kHz, 350 kHz to 450 kHz, 450 kHz to 550 kHz, 550 kHz to 650 kHz, 650 kHz to 750 kHz, 750 kHz to 800 kHz, or 800 kHz to 1000 kHz. When the frequency range is between 200 KHz and 450 KHz, the device operates in relatively low frequency so it is less risky to produce biological heat for better safety. On the other hand, when the frequency range is between 550 kHz and 1000 kHz, the generated electric field has greater density so that the resulting electric stimulation has a better performance.

Furthermore, in the present embodiment, one end of the variable resistor 123 is coupled to the inverting input terminal In1 of the amplifier 122 and the other end is coupled to the output terminal Out of the amplifier 122. Accordingly, the variable resistor 123 and the amplifier 122 form a negative feedback configuration. The amount of gain of the amplifier 122 is adjusted in accordance with the change of the resistance value of the variable resistor 123, and the control unit 11 adjusts the resistance value of the variable resistor 123 in accordance with the electrical stimulation parameters or setting and thereby changes the gain of the amplifier 122, so that the voltage of the stimulation signal S1 can be within a pre-set range.

Please also refer to FIG. 3C, which is a waveform diagram of the frequency signal. In the present embodiment, the frequency signal S2 is a continuous square wave and is emitted in an intermittent manner. That is, a square wave signal of a high frequency is emitted for a period of time TD (hereinafter referred to as a pulse wave width TD) after each pulse wave period TP. It is noted that the frequency of the square wave signal of the high frequency in FIG. 3C is only indicative, and the actual case frequency should be higher. The square wave signal of the high frequency has a pulse frequency between 0 and 1 KHz, and in a preferred embodiment, the square wave signal of the high frequency may have a pulse frequency between 1 and 100 Hz. In the present embodiment, the square wave signal of the high frequency has a pulse frequency of 2 Hz. In addition, the pulse wave width TD (duration) is between 1 and 250 ms. In a preferred embodiment, the pulse wave width TD may be between 10 and 100 ms. In the present embodiment, the pulse width TD is 25 ms.

It is also noted that, in another embodiment of a voltage-driven electrical stimulation device, in order to prevent the patient from feeling discomfort due to sudden electrical stimulation, at the beginning of treatment, after the voltage-driven electrical stimulation device is opened by a medical staff or user to activate the electrical stimulation device power supply, the medical staff or the user can manually turn the knob, or the electrical stimulation device itself can control the way, to make the voltage of the electrical stimulation signal S1 is slowly ramped from 0V at the beginning to the target voltage value. The absolute value of the target voltage value can range from 3V to 12V. The speed of the electrical stimulation signal S1 voltage increase is controlled to not exceed 1V per second. Alternatively, for a current-driven electrical stimulation device, the current can slowly increase from 0 mA to the target current at the beginning of treatment. The absolute value of the target current range can be between 0.5 uA and 50 mA. The rate of current stimulation of the electrical stimulation signal S1 can be controlled to not exceed 5 mA per second (preferably not more than 1 mA per second). When the electrical stimulation signal S1 is turned off after the end of the treatment, it is not necessary to perform a relative current or voltage ramp-down step (i.e., the absolute value of the current or voltage is gradually reduced). In a preferred embodiment, the target current value is 25 mA.

Figure 4A:
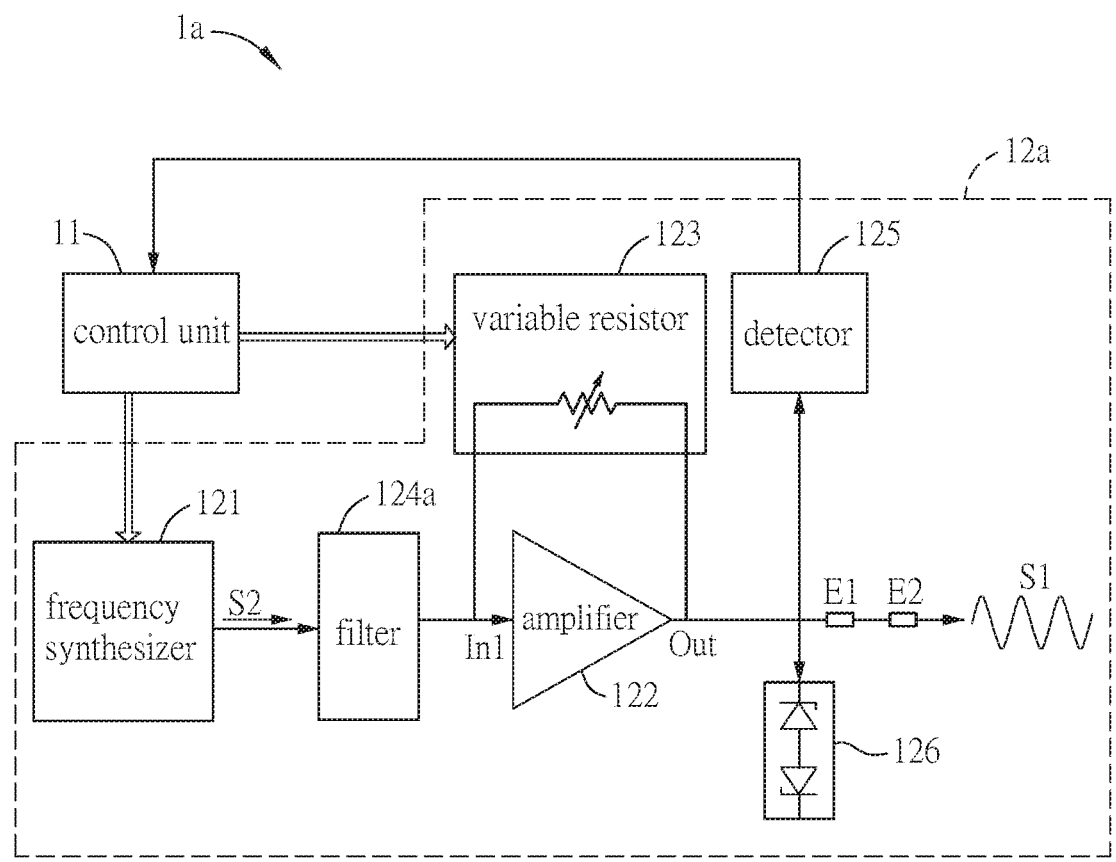
FIG. 4A is a block diagram showing an electrical stimulation device according to another embodiment.
Figure 4B:
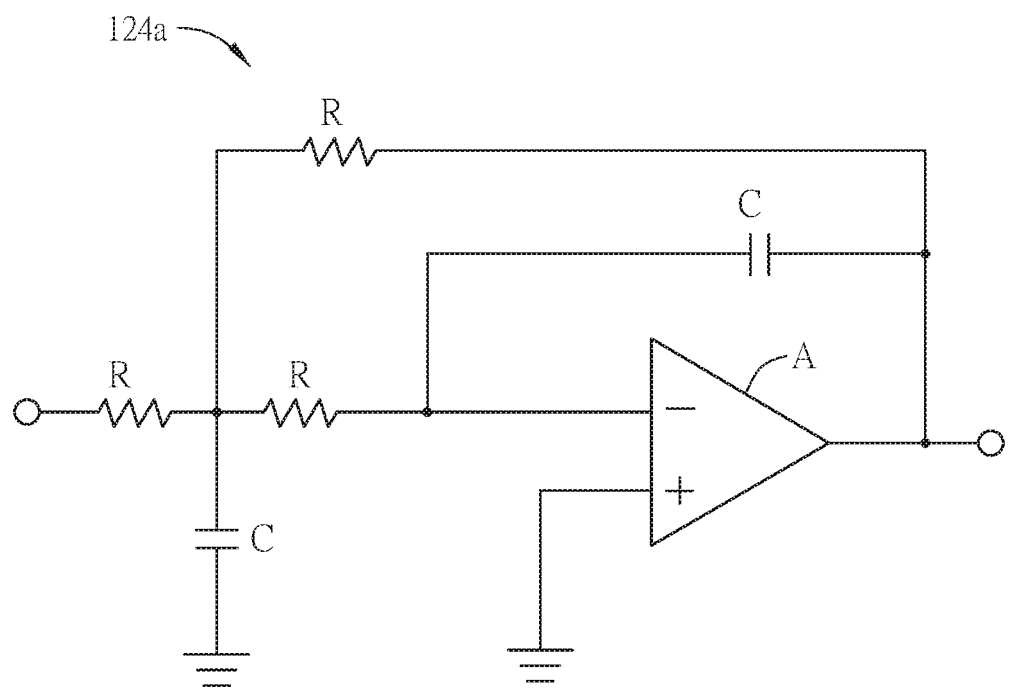
FIG. 4B is a schematic diagram showing the filter of the electrical stimulation device in FIG. 4A.

Please refer to FIGS. 4A and 4B, wherein FIG. 4A is a block diagram of another electrical stimulation device of the present invention, and FIG. 4B is a schematic view of the filter shown in FIG. 4A. In the present embodiment, the electrical stimulation unit 12a further includes a filter 124a coupled between the frequency synthesizer 121 and the amplifier 122. In other words, the filter 124a is coupled to the inverting input terminal In1. The filter 124a of the present embodiment is a low-pass filter with a cutoff frequency of 1000 kHz to filter out the high frequency portion of the frequency signal S2 so that the signal input to the amplifier 122 is 1000 kHz or less, thereby to match the default frequency range of the electrical stimulation signal S1 (100 kHz to 1000 kHz). As shown in FIG. 4B, the filter 124a can be implemented by coupling the capacitor C and the complex resistance R by another amplifier A. Herein, the filter 124a is a second-order low-pass filter, but the present invention is not limited thereto.

Please refer to FIG. 3A. It should be noted that the electric power source of the electrical stimulation device 1 may also be a built-in battery that is coupled to a power management unit (not shown) and the power management unit may provide power of the battery to the control unit 11 and the electrical stimulation unit 12. Alternatively, the power source may be an external power supply unit, such as a wireless charging unit having a coil and a rectifier. The coil couples to a magnetic field generated by a wireless power supply device to produce an induced current, and the rectifier rectifies the induced current to a DC current and outputs the DC current to the power management unit of the electrical stimulation device 1, to supply the power to the control unit 11 and the electrical stimulation unit 12. In addition, the power management unit may include a voltage invertor that reverses the polarity of the received voltage to provide the reverse operating voltage required by the amplifier 122.

Referring again to FIG. 4A, the electrical stimulation unit 12a may further include a detector 125 coupled to the control unit 11 and the amplifier 122, and the detector 125 detects the electrical stimulation signal S1. In the present embodiment, the detector 125 is coupled to the output terminal Out of the amplifier 122. The control unit 11 may detect the voltage of the electrical stimulation signal S1, for example, whether or not the waveform of the output terminal Out is matched with a preset waveform (for example, 3V to 12V as described above). When the waveform of the electrical stimulation signal S1 deviates from the preset waveform, the control unit 11 may modify the electrical stimulation parameter in real time, for example, by changing the resistance value of the variable resistor 123 such that the electrical stimulation signal S1 conforms to the electrical stimulation signal S1, so that the electrical stimulation signal S1 conforms to the aforementioned voltage range, and thus to avoid outputting an electrical stimulation signal S1 with incorrect voltage.

In addition, in some embodiments, the electrical stimulation unit 12a may further include a surge protector 126 that couples the amplifier 122, for example, to the output terminal Out of the coupling amplifier 122. In one embodiment, the surge protector 126 may be, for example, a zener diode, a transient duration suppression (TVS) diode, or a bidirectional ESD protection diodes. International Organization for Standardization International Standard No. ISO 14708-3 stipulates that active implantable medical devices (AIMDs) implanted in an individual must not produce a permanent influences to a patient who uses a defibrillator. Thus, disposition of the surge protector 126 may limit the high voltage of the pulses (e.g., 1000 V) provided by the defibrillator to a relative low voltage which is acceptable to the human body, such as 5V, so as to prevent nerve damage due to the high voltage pulse, and to the electric stimulation unit 12a is also prevented from outputting an electrical stimulation signal S1 of excessively high voltage at the time of abnormality, which causes damage to the patient.

In addition, in other embodiments, one end of the variable resistor 123 may be only coupled to the input terminal, while the other end receives the frequency signal S2. The control unit 11 can change the voltage of the frequency signal S2 in a voltage-dividing manner by altering the resistance value of the variable resistor 123, thereby changing the voltage of the electrical stimulation signal S1 outputted from the amplifier 122.

In addition, in some embodiments, one end of the variable resistor 123 may be only coupled to the output Out and the other end coupled to the ground, so that the control unit 11 can also change the voltage of the stimulation signal S1 by altering the resistance of the variable resistor 123.

In general, the neurons of the central nervous system mainly consist of sensory neurons and motor neurons. The high frequency electrical stimulation signal does not agitate the sensory neurons or the sensory neurons. That is, the human body will not feel such high frequency electrical stimulation. Thus, when a patient is treated with a high frequency electrical stimulation signal, it may occur that the patient thinks he is not receiving any treatment because no electrical stimulation is sensed. In order to solve this problem, during the course of treatment, some low-frequency electrical stimulation signals can be added to make the patient feel the treatment process, and thus be more relieved to accept treatment. In addition, by low frequency electrical stimulation signals, it is also possible to assist the medical personnel to position the electrodes or devices of during the implantation of the electrical stimulation device, so as to prevent the user from not finding the offset of the position of the electrical stimulation device until implantation is complete.

Figure 5A:
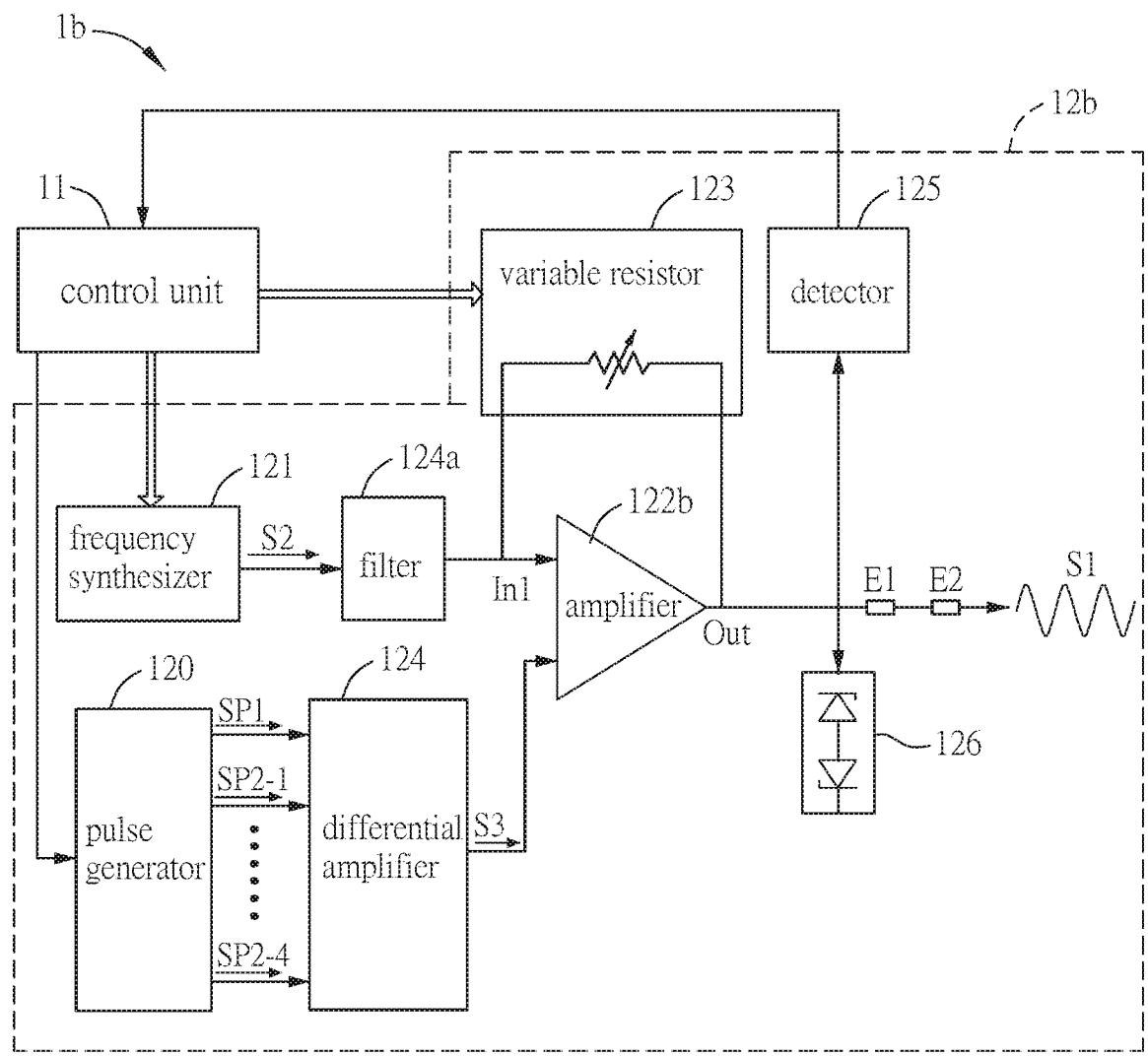
FIG. 5A is a block diagram showing an electrical stimulation device according to another embodiment.
Figure 5B:
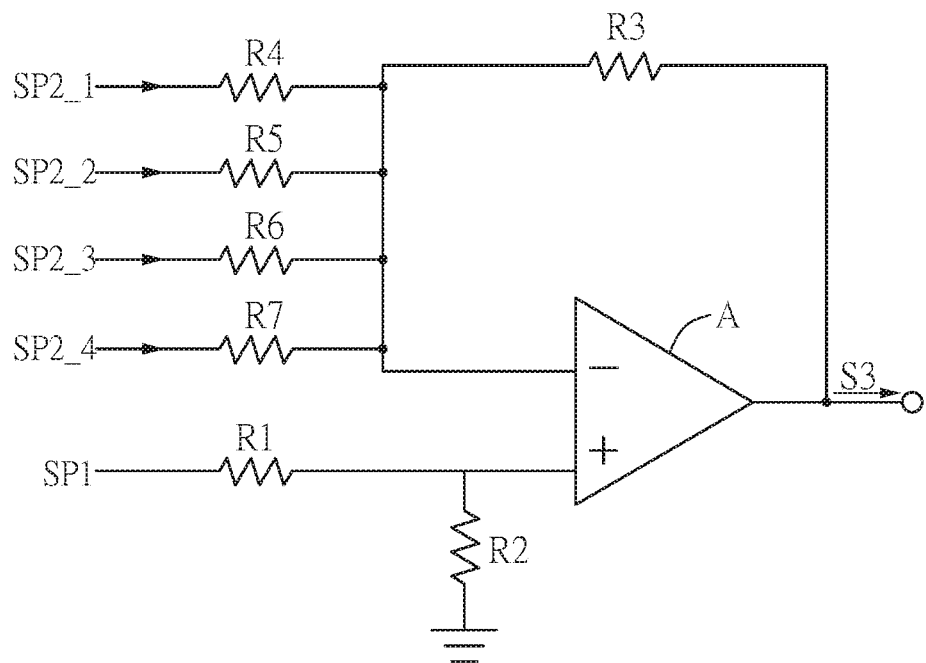
FIG. 5B is a circuit block diagram showing the differential amplifier of the electrical stimulation device in FIG. 5A.
Figure 5C:
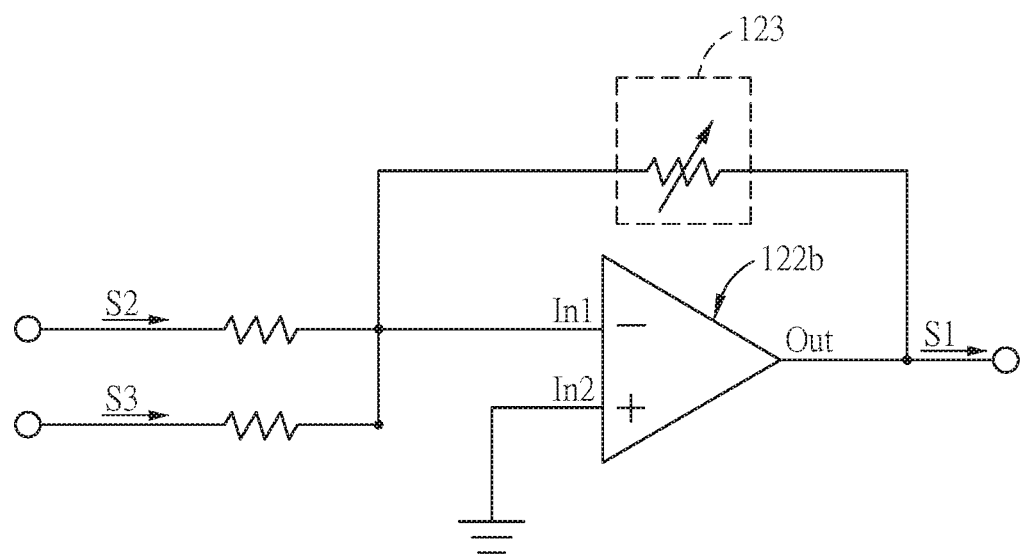
FIG. 5C is a circuit block diagram showing the amplifier of the electrical stimulation device in FIG. 5A.

FIG. 5A is a schematic block diagram of another embodiment of the electrical stimulation device of the present invention, and FIG. 5B is a circuit diagram of a differential amplifier of the electrical stimulation device of FIG. 5A. FIG. 5C is a circuit diagram of the amplifier of the electrical stimulation device of FIG. 5A. The structure of the electrical stimulation device 1b is substantially the same as that of the electrical stimulation device 1a, except that the electric stimulation unit 12b of the electrical stimulation device 1b further includes a pulse generator 120 and a differential amplifier 124 and the amplifier 122b of the stimulation device 1b is a summing amplifier. The pulse generator 120 generates a set of pulse wave signals, respectively, and after the addition of the differential amplifier 124 to generate the biphasic pulse wave signal S3. Since the biphasic pulse wave signal S3 is essentially a low-frequency signal, it is possible to cause the patient to feel the electrical stimulation (via sensory neurons) or cause muscle contraction (via motor neurons) after adding the electrical stimulation signal S1 by the amplifier 122b. In the biphasic pulse signal S3, the charge balance is required between the positive phase signal portion and the negative phase signal portion in order to reduce the harm to the nerve caused by the electrical stimulation therapy. In the present invention, the charge balance is defined as that "the absolute value of the sum of the integrated value obtained by integrating the positive-phase signal portion with respect to time and the integrated value obtained by integrating the negative-phase signal portion with respect to time is not larger than one-tenth of the integrated value obtained by integrating the positive-phase signal portion with respect to time."

Please refer to FIGS. 5A and 5B. FIG. 5B is a circuit diagram of a preferred embodiment of the differential amplifier 124 of the electrical stimulation device of the present invention. The differential amplifier 124 is an operational amplifier (OPA) having an inverting input terminal In1, a non-inverting input terminal In2, and an output terminal Out. The pulse generator 120 generates a first pulse wave signal SP1 and at least one of the second pulse wave signals SP2_1 to SP2_4. In the present embodiment, the first pulse signal SP1 of the pulse generator 120 is coupled to the non-inverting input terminal In2 of the differential amplifier 124 through a resistor R1, and the non-inverting input terminal In2 of the differential amplifier 124 is coupled to ground through a resistor R2. A resistor R3 is coupled between the output terminal of the differential amplifier 124 and the non-inverting input terminal In2. The second pulse wave signals SP2_1 to SP2_4 of the pulse generator 120 are respectively coupled to the inverting input terminal In1 of the differential amplifier 124 through resistors R4 to R7. As a result, the biphasic pulse signal S3 can be calculated by the following formula:

$$S3=SP1 \cdot (R2/(R1+R2)) \cdot (R3/(R4//R5//R6//R7))+SP2\_1 \\ (-R3/R4)+SP2\_2(-R3/R5)+SP2\_3(-R3/R6)+ \\ SP2\_4(-R3/R7)$$

In the present embodiment, R1=R2=R3, R4=R5=8*R1, R6=4*R1, R7=2*R1. Therefore, the above equation becomes:

$$S3=SP1+SP2\_1 \cdot (-1/8)+SP2\_2 \cdot (-1/8)+SP2\_3 \cdot (-2/8)+ \\ SP2\_3 \cdot (-4/8)$$

As can be seen from the above equation, the positive phase signal portion of the biphasic pulse wave signal S3 is constituted by the first pulse wave signal SP1, and the negative phase signal portion is constituted by the second pulse wave signals SP2_1 to SP2_4. As a result, the electrical stimulation device of the present invention can adjust the waveform of the negative phase signal portion by controlling the second pulse wave signals SP2_1 to SP2_4.

Figure 6A:
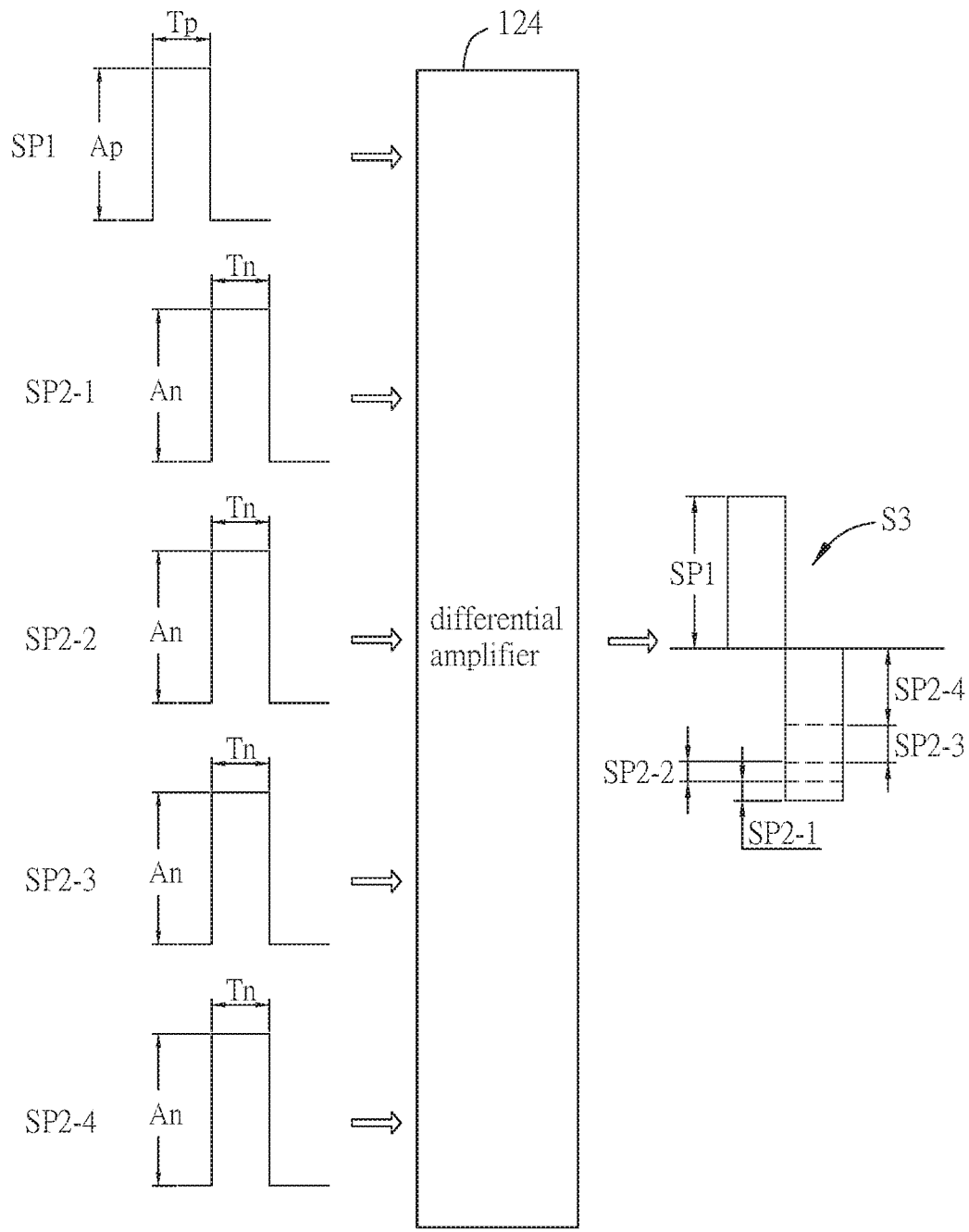
FIGS. 6A to 6D are schematic diagrams showing the waveforms of the biphasic pulse signals.

For example, reference is made to FIGS. 6A to 6D, which are waveform diagrams of preferred embodiments of the biphasic pulse wave signal. In FIG. 6A, the first pulse signal SP1 has an amplitude Ap and a wave width Tp; the second pulse wave signals SP2_1 to SP2_4 have an amplitude An and a wave width Tn. In the present embodiment, the amplitude Ap is equal to the amplitude An and is between 3 V and 12 V, the wave width Tp is equal to the wave width Tn, and is between 50 μs and 100 μs. As a result, when the second pulse signal SP2_1 passes through the differential amplifier 124, it becomes inverted and the amplitude becomes ⅛·Ap. When the second pulse signal SP2_2 passes through the differential amplifier 124, it becomes inverted and the amplitude becomes ⅛·Ap. When the second pulse signal SP2_3 passes through the differential amplifier 124, it becomes inverted and the amplitude becomes ¼·Ap. When the second pulse signal SP2_4 passes through the differential amplifier 124, it becomes inverted and the amplitude becomes ½·Ap. After the second pulse signals SP2_1 to SP_4 are added via the differential amplifier 124, the amplitude is just equal to Ap and becomes opposite phase to the first pulse signal SP1.

Figure 6B:
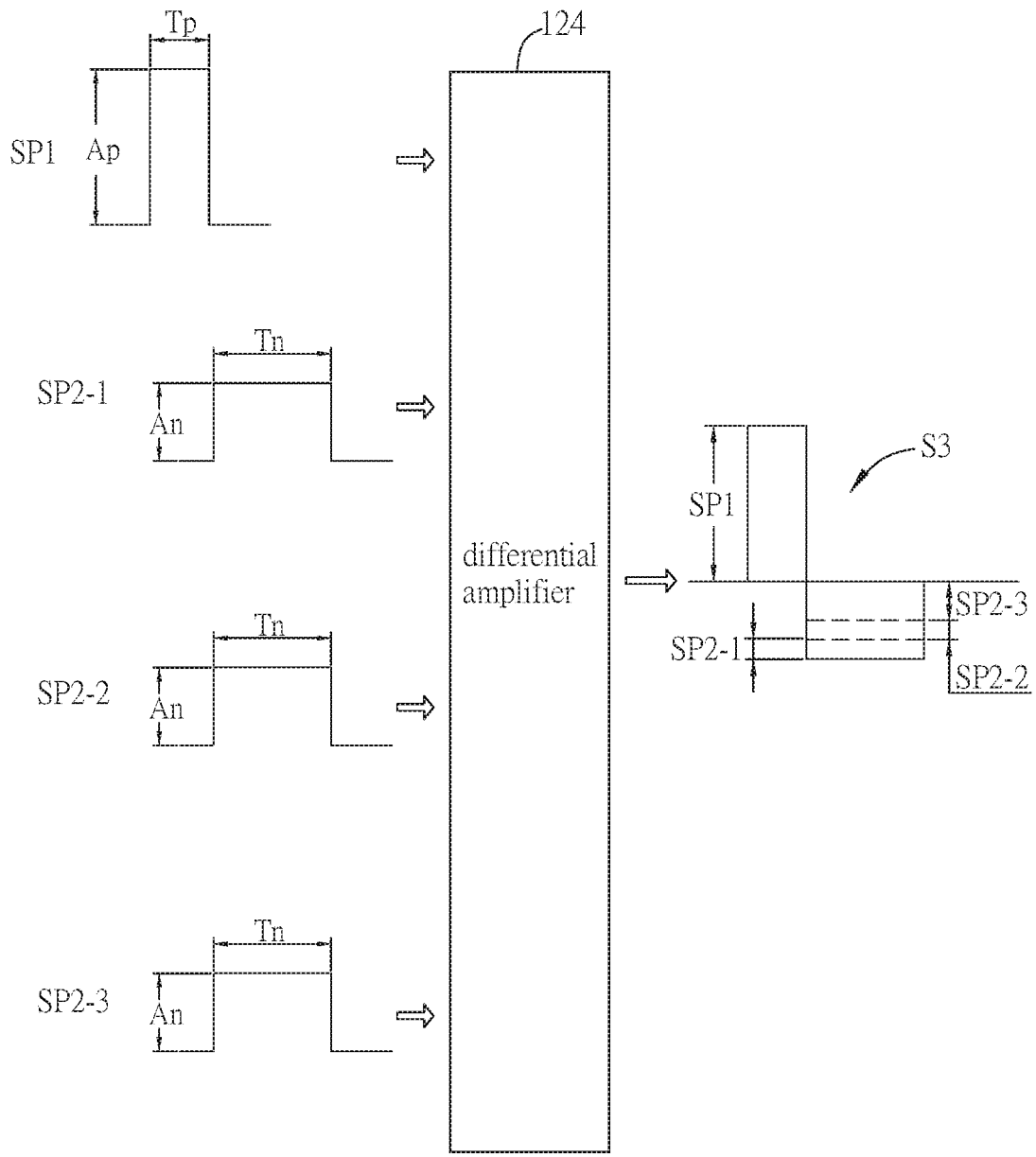

In FIG. 6B, the first pulse signal SP1 has an amplitude Ap and a wave width Tp. The second pulse wave signals SP2_1 to SP2_3 each have an amplitude An and a wave width Tn. In this embodiment, the amplitude Ap is equal to the amplitude An, and between 3 V and 12 V, and the wave width Tn is equal to twice the wave width Tp, and is between 50 μs and 100 μs, in order to achieve charge balance. As a result, when the second pulse signal SP2_1 passes through the differential amplifier 124, it becomes inverted and the amplitude becomes ⅛·Ap. When the second pulse signal SP2_2 passes through the differential amplifier 124, it becomes inverted and the amplitude becomes ⅛·Ap. When the second pulse signal SP2_3 passes through the differential amplifier 124, it becomes inverted and the amplitude becomes ¼·Ap. After the second pulse signal SP2_1 to SP_4 is added via the differential amplifier 124, the amplitude is exactly equal to ½·Ap, and becomes opposite phase to the first pulse signal SP1. Since the wave width Tn is equal to twice the wave width Tp, the charge balance is still satisfied.

Figure 6C:
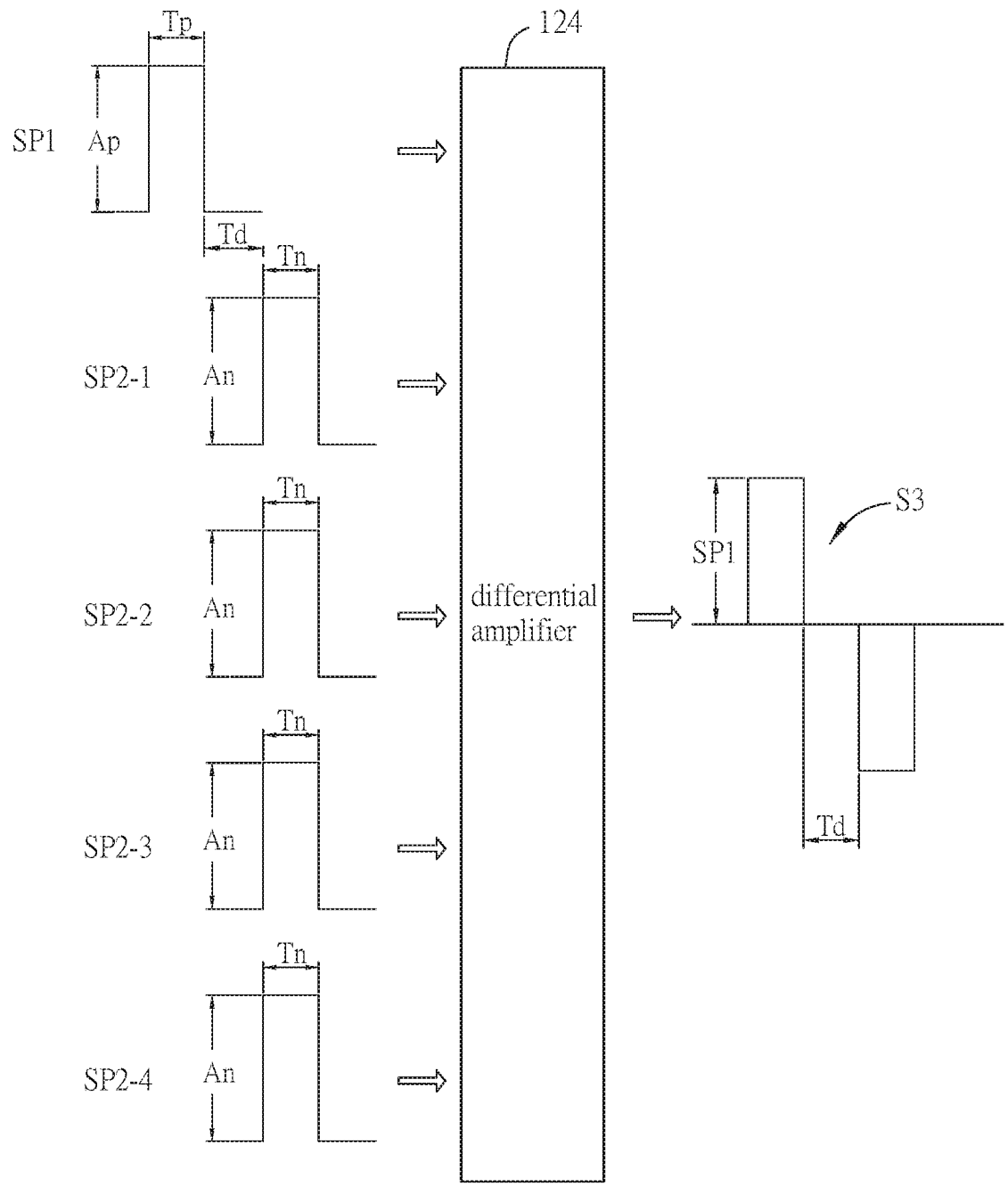

In FIG. 6C, the first pulse signal SP1 has an amplitude Ap and a wave width Tp. The second pulse wave signals SP2_1 to SP2_4 each have an amplitude An and a wave width Tn. In the present embodiment, the amplitude Ap is equal to the amplitude An, the width Tp is equal to the width Tn, and the first pulse wave signal SP1 and any one of the second pulse wave signals SP2_1 to SP2_4 have a time difference Td. As a result, when the second pulse signal SP2_1 passes through the differential amplifier 124, it becomes inverted, and the amplitude becomes ⅛·Ap. When the second pulse signal SP2_2 passes through the differential amplifier 124, it becomes inverted and the amplitude becomes ⅛·Ap. When the second pulse signal SP2_3 passes through the differential amplifier 124, it becomes inverted and the amplitude becomes ¼·Ap. When the second pulse signal SP2_4 passes through the differential amplifier 124, it becomes inverted and the amplitude becomes ½·Ap. After the second pulse signals SP2_1 to SP_4 are added via the differential amplifier 124, the amplitude is just equal to Ap and becomes opposite phase to the first pulse signal SP1.

Figure 6D:
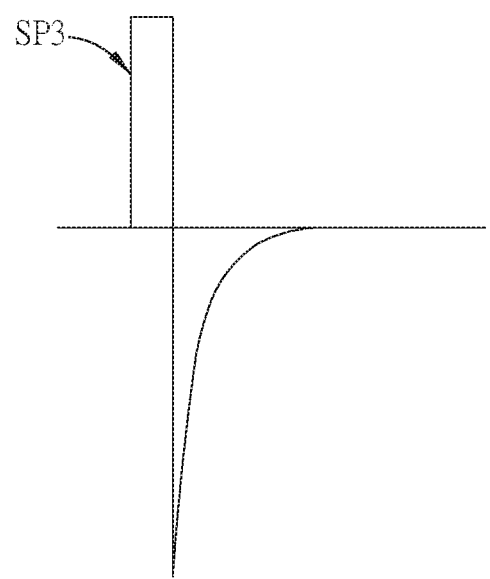

It is noted that, in another embodiment, the capacitor C (not shown) may be connected in series with the resistor R3. This allows the negative phase signal portion of the biphasic pulse wave signal S3 to be attenuated (as shown in FIG. 6D) so that the biphasic pulse signal S3 can be applied to different patients of different constitutions.

Figure 7:
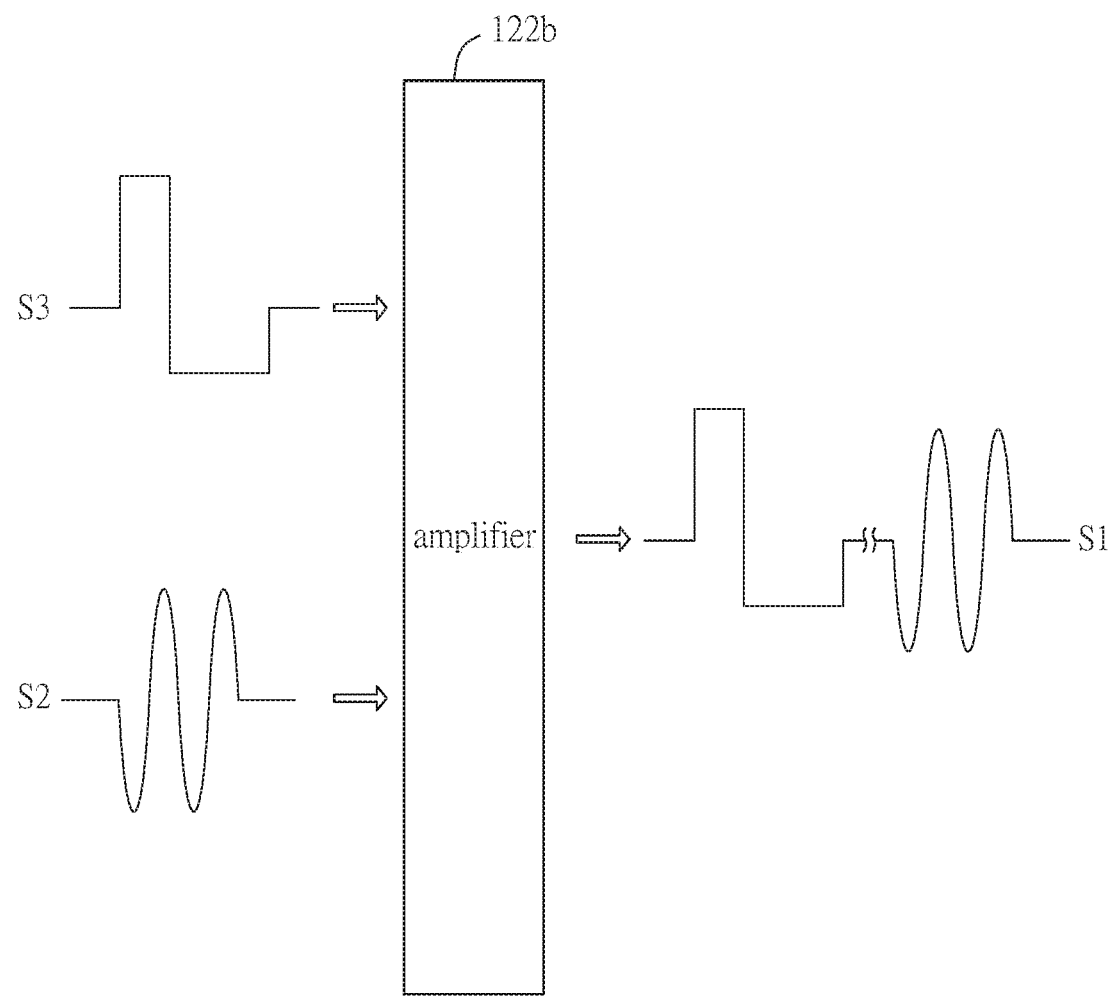
FIG. 7 is a schematic diagram showing the electrical stimulation signal according to one embodiment.
Figure 8C:
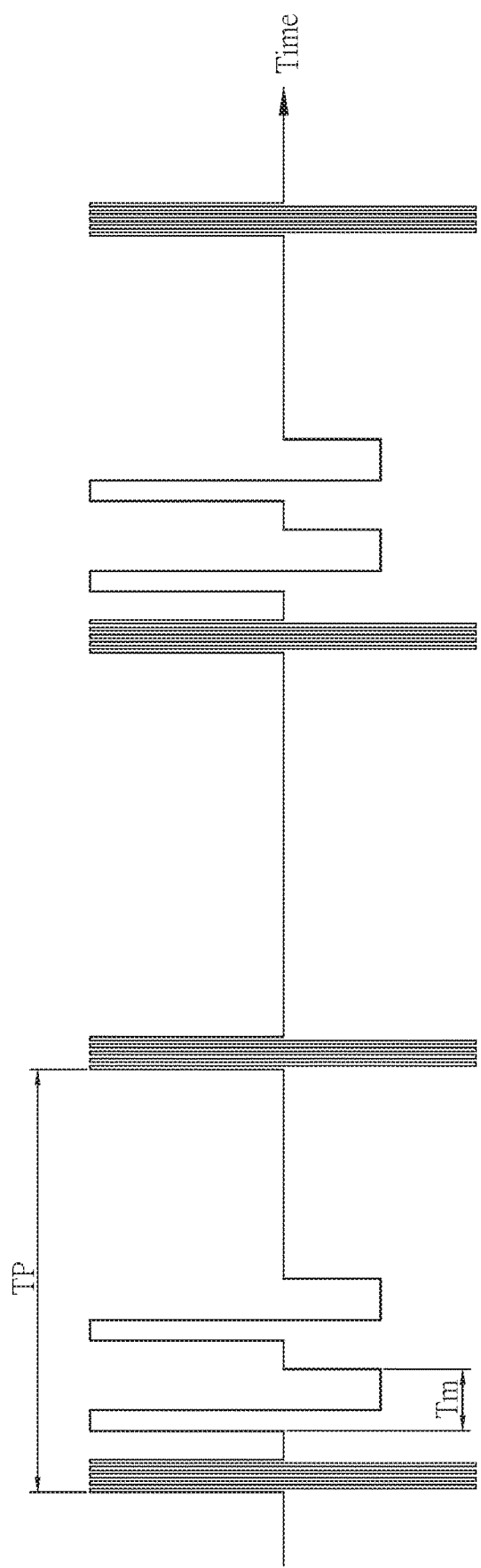
Figure 8D:
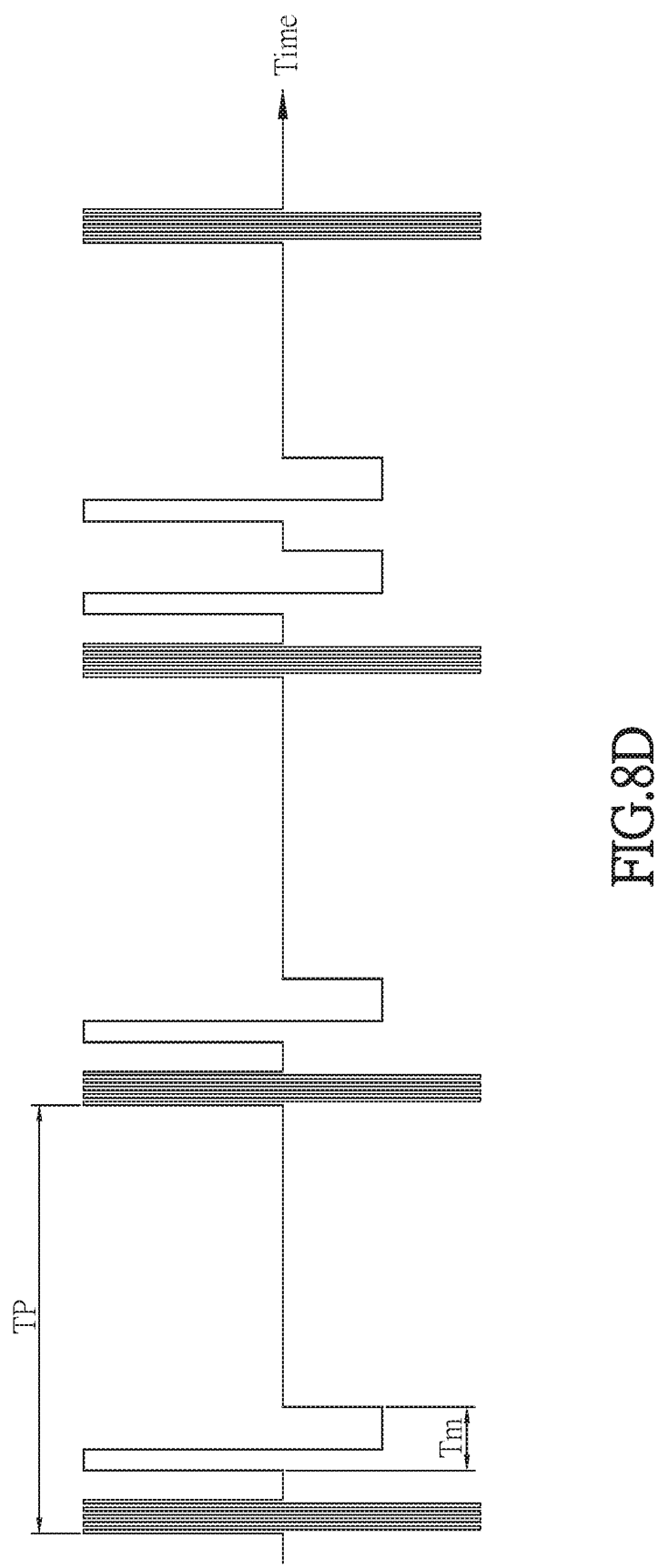

Please refer to FIG. 5C. In the present embodiment, the amplifier 122b is a summing amplifier coupled to the differential amplifier 124, the variable resistor 123, and the frequency synthesizer 121. The amplifier 122b is an operational amplifier (OPA) having an inverting input terminal In1, a non-inverting input terminal In2, and an output terminal Out. The output of the frequency synthesizer 121 is coupled to one of the inputs (inverting input In1 or inverting input In2) of the amplifier 122b and the output of the differential amplifier 124 is also coupled to the same input of the amplifier 122b. For example, in the present embodiment, the frequency synthesizer 121 is coupled to the inverting input terminal In1 and the noninverting input terminal In2 is connected to ground. In this way, since the output voltage of the frequency synthesizer 121 is relative low (about 650 mV), in the present embodiment, the voltage of the frequency signal S2 outputted from the frequency synthesizer 121 is amplified to 3 V to 12 V by the amplifier 122b, so as to conform to the voltage setting of the electrical stimulation signal S1. The amplifier 122b adds the frequency signal S2 and the biphasic pulse wave signal S3 (for example, as shown in FIG. 6B) to obtain the electrical stimulation signal S1 whose waveform is as shown in FIG. 7.

It is noted that the time difference between the biphasic pulse wave signal S3 and the frequency signal S2 needs to be maintained to be at least 2 micro-seconds. In addition, the biphasic pulse wave signal S3 may be configured to be issued at least once before and/or after the course of treatment to indicate the beginning and/or the end of the patient, during the electrical stimulation therapy. In another practicing mode, such as during the process of the implantation of the electrical stimulation device, the biphasic pulse wave signal S3 may also be an intermittent periodic signal. For example, the pulse generator 120 may control the generation of the pulse wave signals SP1, SP2_1 to SP2_4, such that the differential amplifier intermittently generates four biphasic pulse wave signals S3 during the four pulse wave periods TP of the frequency signal S2. Each biphasic pulse signal S3 has a duration Tm and is spaced by at least 2 micro-seconds. Thus, the electrical stimulation signal S1, which is synthesized by the frequency signal S2 and the biphasic pulse wave signal S3 transmitted through the amplifier 122b, is as shown in FIGS. 8A to 8D. FIGS. 8A to 8D are waveform diagrams in different embodiments of the electrical stimulation signal of the present invention. FIGS. 8A to 8D are merely illustrative of the possible waveforms of the electrical stimulation signal S1 synthesized by the frequency signal S2 and the biphasic pulse wave signal S3. The waveform of the electrical stimulation signal S1 may also have other variations. As long as the pulse generator 120 controls the occurrence of the biphasic pulse wave signal S3 at a frequency no greater than the pulse wave frequency of the frequency signal S2, the waveform of the finally generated electrical stimulation signal S1 is within the scope of the present invention.

In summary, the electrical stimulation device of the present invention adjusts the frequency of the output signal via the frequency synthesizer and adjusts the voltage range of the output signal through the amplifier and the variable resistor so that the first electrode and the second electrode generate an electric field whose strengths ranges from 100 V/m to 5000 V/m. In this way, the electrical stimulation device can provide the electric stimulation signal of the different electric field strength to the patient according to the different application way, so as to give an appropriate electrical stimulation treatment to the patient. In another aspect, via the pulse generator and the differential amplifier, the electrical stimulation device of the present invention adds the pulse waves with the same total amount of electrical charges to a biphasic pulse wave with charge balance pulse generator, so as to avoid the harm to the nerve caused by the electrical stimulation signal.

Although the invention has been described with reference to specific embodiments, this description is not meant to be construed in a limiting sense. Various modifications of the disclosed embodiments, as well as alternative embodiments, will be apparent to persons skilled in the art. It is, therefore, contemplated that the appended claims will cover all modifications that fall within the true scope of the invention.

What is claimed is:

1. An electrical stimulation device for electrically stimulating at least one target zone of an organism, comprising
    a control unit; and
    an electrical stimulation unit including:
    a frequency synthesizer which is coupled to the control unit and configured to generate a frequency signal;
    a summing amplifier which is coupled to the frequency synthesizer;
    a variable resistor which comprises a resistance and is coupled to the control unit and the summing amplifier;
    at least one first electrode and at least one second electrode, wherein the first electrode and the second electrode are coupled to the summing amplifier;
    a pulse generator which is coupled to the control unit and configured to generate a plurality of pulse signals, wherein the plurality of pulse signals include a first pulse wave signal and a second pulse wave signal, a time difference between the first pulse wave signal and the second pulse wave signal is at least 2 microseconds; and
    a differential amplifier which is coupled to the pulse generator and the summing amplifier, and configured to output a biphasic pulse signal according to the plurality of pulse signals,
    wherein the summing amplifier is configured to output an electrical stimulation signal according to the biphasic pulse signal, the frequency signal of the frequency synthesizer and the resistance of the variable resistor to impel the first electrode and the second electrode to generate an electric field, the electric field covers the target zone, and the electric field strength ranges from 100 V/m to 5000 V/m.

2. The electrical stimulation device according to claim 1, wherein the frequency synthesizer is coupled to an input of the summing amplifier.

3. The electrical stimulation device according to claim 2, wherein the variable resistor is coupled to the input of the summing amplifier.

4. The electrical stimulation device according to claim 2, wherein the variable resistor is coupled to an output of the summing amplifier.

5. The electrical stimulation device according to claim 3, wherein the variable resistor is coupled to an output of the summing amplifier.

6. The electrical stimulation device according to claim 1, wherein the electrical stimulation unit further comprises a filter which is coupled between the frequency synthesizer and the summing amplifier.

7. The electrical stimulation device according to claim 1, wherein the electrical stimulation unit further comprises a surge protector which is coupled to the summing amplifier.

8. The electrical stimulation device according to claim 1, wherein the electrical stimulation device is an implanted electrical stimulation device.

9. The electrical stimulation device according to claim 1, wherein the frequency of the electrical stimulation signal ranges from 200 KHz to 1000 KHz.

10. The electrical stimulation device according to claim 1, wherein the voltage of the electrical stimulation signal is biphasic, and its absolute value is between 3V and 12V.

11. The electrical stimulation device according to claim 1, wherein the biphasic pulse signal comprises a positive phase signal portion, a negative phase signal portion, and an absolute value of a sum of the integrated value of the positive phase signal portion with respect to time and the integrated value of the negative phase signal portion with respect to time is not more than one tenth of the integrated value of the positive phase signal portion with respect to time.

12. The electrical stimulation device according to claim 11, wherein the first pulse wave signal is a positive pulse constituting the positive phase signal portion of the biphasic pulse signal, and the second pulse wave signal is a positive pulse constituting the negative phase signal portion of the biphasic pulse signal by inverting.

13. The electrical stimulation device according to claim 1, wherein the electrical stimulation unit further comprises:
    a detector coupled to the control unit and the summing amplifier, and configured to detect the electrical stimulation signal.

14. The electrical stimulation device according to claim 13, wherein the control unit detects whether the waveform of the electrical stimulation signal detected by the detector is matched with a preset waveform, the control unit modifies the electrical stimulation signal when the waveform of the electrical stimulation signal deviates from the preset waveform.

15. A method applied to electrically stimulate a target zone of an organism by an implanted electrical stimulation device, wherein the implanted electrical stimulation device comprises a frequency synthesizer, a variable resistor, at least a first electrode, at least a second electrode, the method comprising:
    generating a frequency signal by the frequency synthesizer;
    generating a plurality of pulse signals, wherein the plurality of pulse signals include a first pulse wave signal and a second pulse wave signal, a time difference between the first pulse wave signal and the second pulse wave signal is at least 2 micro-seconds;

outputting a biphasic pulse signal according to the plurality of pulse signals;

outputting an electrical stimulation signal according to the biphasic pulse signal, the frequency signal and the resistance of the variable resistor; and delivering the electrical stimulation signal by the first electrode and the second electrode to generate an electrical field between the first electrode and the second electrode to electrically stimulate the target zone, wherein the electric field covers the target zone, and strength of the electric field ranges from 100 V/m to 5000 V/m.

16. The method according to claim 15, wherein the frequency of the electrical stimulation signal ranges from 200 KHz to 1000 KHz.

17. The method according to claim 15, wherein the biphasic pulse signal comprises a positive phase signal part, a negative phase signal part, and an absolute value of a sum of the integrated value of the positive phase signal portion with respect to time and the integrated value of the negative phase signal portion with respect to time is not more than one tenth of the integrated value of the positive phase signal portion with respect to time.

18. The method according to claim 17, wherein the first pulse wave signal is a positive pulse constituting the positive phase signal portion of the biphasic pulse signal, and the second pulse wave signal is a positive pulse constituting the negative phase signal portion of the biphasic pulse signal by inverting.

19. The method according to claim 15, wherein the implanted electrical stimulation device further comprises a detector, and the method further comprises:

by a control unit, detecting whether the waveform of the electrical stimulation signal detected by the detector is matched with a preset waveform;

by the control unit, modifying the electrical stimulation signal when the waveform of the electrical stimulation signal deviates from the preset waveform.

* * * * *